United States Patent
Memic et al.

(10) Patent No.: US 12,303,618 B2
(45) Date of Patent: May 20, 2025

(54) OXYGEN-GENERATING CRYOGELS

(71) Applicant: Northeastern University, Boston, MA (US)

(72) Inventors: Adnan Memic, Macomb, MI (US); Sidi A. Bencherif, Boston, MA (US); Michail Sitkovsky, Boston, MA (US); Thibault Colombani, Boston, MA (US); Stephen Hatfield, Peabody, MA (US)

(73) Assignee: Northeastern University, Boston, MA (US)

( * ) Notice: Subject to any disclaimer, the term of this patent is extended or adjusted under 35 U.S.C. 154(b) by 1005 days.

(21) Appl. No.: 17/266,351

(22) PCT Filed: Aug. 8, 2019

(86) PCT No.: PCT/US2019/045740
§ 371 (c)(1),
(2) Date: Feb. 5, 2021

(87) PCT Pub. No.: WO2020/033713
PCT Pub. Date: Feb. 13, 2020

(65) Prior Publication Data
US 2021/0308334 A1    Oct. 7, 2021

Related U.S. Application Data

(60) Provisional application No. 62/716,132, filed on Aug. 8, 2018.

(51) Int. Cl.
A61L 27/54    (2006.01)
A61L 27/02    (2006.01)
(Continued)

(52) U.S. Cl.
CPC ............. *A61L 27/54* (2013.01); *A61L 27/025* (2013.01); *A61L 27/20* (2013.01); *A61L 27/52* (2013.01);
(Continued)

(58) Field of Classification Search
None
See application file for complete search history.

(56) References Cited

U.S. PATENT DOCUMENTS 9,675,561 B2    6/2017  Bencherif et al.
2009/0170973 A1*  7/2009  Mattiasson ........ B01J 20/28042
                                                521/134
(Continued)

FOREIGN PATENT DOCUMENTS

EP     3011981 A1 *   4/2016   ............. A61L 27/20
WO   WO-9733879 A1 *  9/1997   ............ A61K 31/519

OTHER PUBLICATIONS

Sheikh et al. (Oxygen-Releasing Antioxidant Cryogel Scaffolds with sustained oxygen delivery for tissue engineering applications, ACS Applied Materials and Interfaces—May 2018). (Year: 2018).*
(Continued)

*Primary Examiner* — Carlos A Azpuru
*Assistant Examiner* — Casey S Hagopian
(74) *Attorney, Agent, or Firm* — Foley Hoag LLP; Dana M. Gordon; Tatiana P. Headrick

(57) ABSTRACT

Disclosed are nanocomposite oxygen-generating cryogels and their uses in reducing hypoxia in a biological tissue, such as a tumor. Methods of treating cancer with the disclosed cryogels are also provided.

21 Claims, 31 Drawing Sheets

(51) Int. Cl.
A61L 27/20 (2006.01)
A61L 27/52 (2006.01)

(52) U.S. Cl.
CPC ...... *A61L 2300/11* (2013.01); *A61L 2300/254* (2013.01); *A61L 2300/416* (2013.01)

(56) References Cited

U.S. PATENT DOCUMENTS

2011/0262489 A1  10/2011  Zhao
2014/0178964 A1   6/2014  Mooney et al.
2017/0319394 A1*  11/2017  Chen ................ A61F 13/05
2019/0076373 A1   3/2019  Bencherif et al.

OTHER PUBLICATIONS

Shiekh et al. Oxygen-releasing antioxidant cryogel scaffolds with sustained oxygen delivery for tissue engineering applications, Applied Materials and Interfaces, 10(8):18458-18469 (2018). (Year: 2018).*

Rezaeeyazdi et al. Injectable Hyaluronic Acid-co-Gelatin Cryogels for Tissue-Engineering Applications. Materials (Basel). Aug. 7, 2018;11(8):1374, pp. 1-18. (Year: 2018).*

Batchelor et al. Improved tumor oxygenation and survival in glioblastoma patients who show increased blood perfusion after cediranib and chemoradiation, PNAS, Nov. 19, 2013, vol. 110, No. 47, 19059-19064. (Year: 2013).*

Hill et al. "Designing Scaffolds to Enhance Transplanted Myoblast Survival and Migration", Tissue Engineering, 12(5): 1295-1304 (2006). (Year: 2006).*

Alemdar et al., "Oxygen-Generating Photo-Cross-Linkable Hydrogels Support Cardiac Progenitor Cell Survival by Reducing Hypoxia-Induced Necrosis," ACS Biomater. Sci. Eng. 3(9):1964-1971 (2016).

International Search Report and Written Opinion for International Application No. PCT/US2019/045740 dated Nov. 21, 2019.

Shiekh et al., "Oxygen-Releasing Antioxidant Cryogel Scaffolds with Sustained Oxygen Delivery for Tissue Engineering Applications," ACS Applied Materials and Interfaces, 10(8):18458-18469 (2018).

Hill et al., "Designing Scaffolds to Enhance Transplanted Myoblast Survival and Migration," Tissue Engineering, 12(5): 1295-1304 (2006).

* cited by examiner

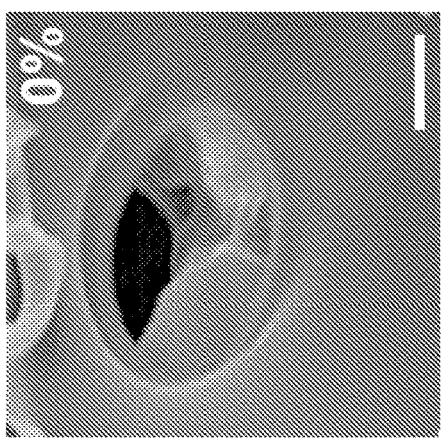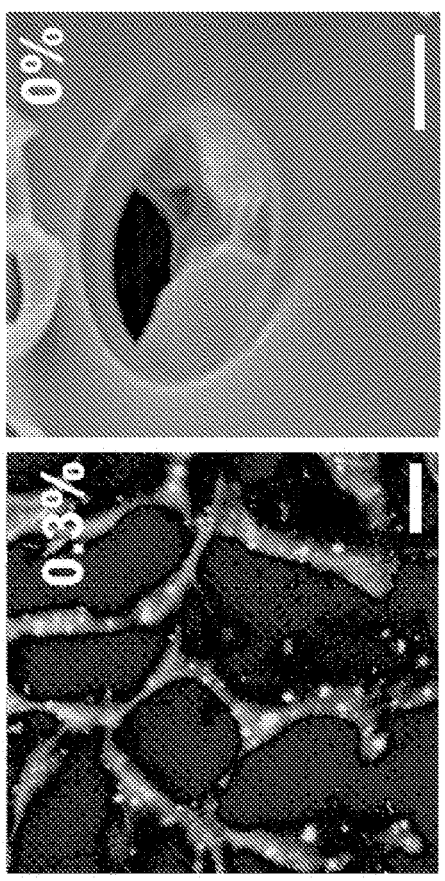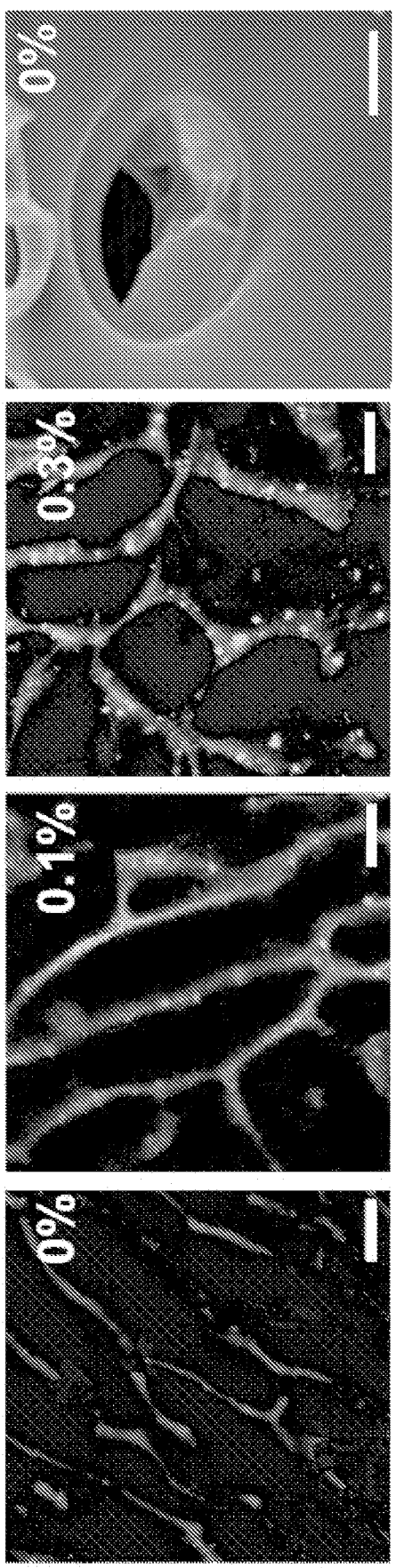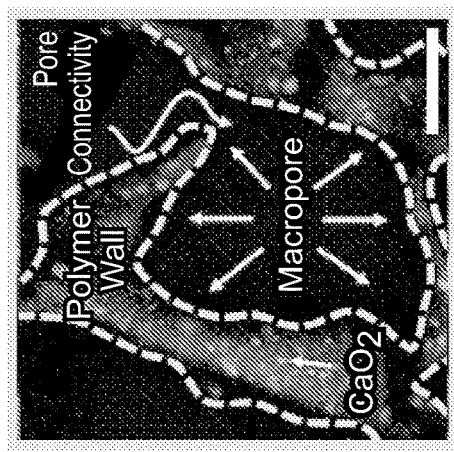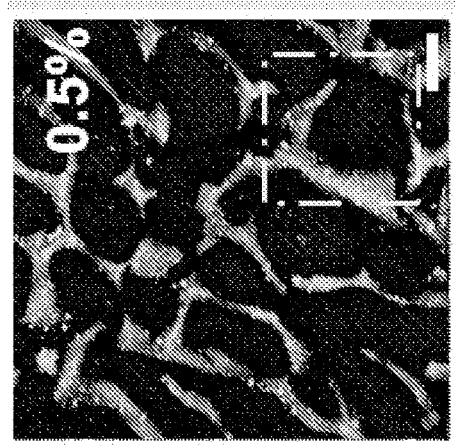

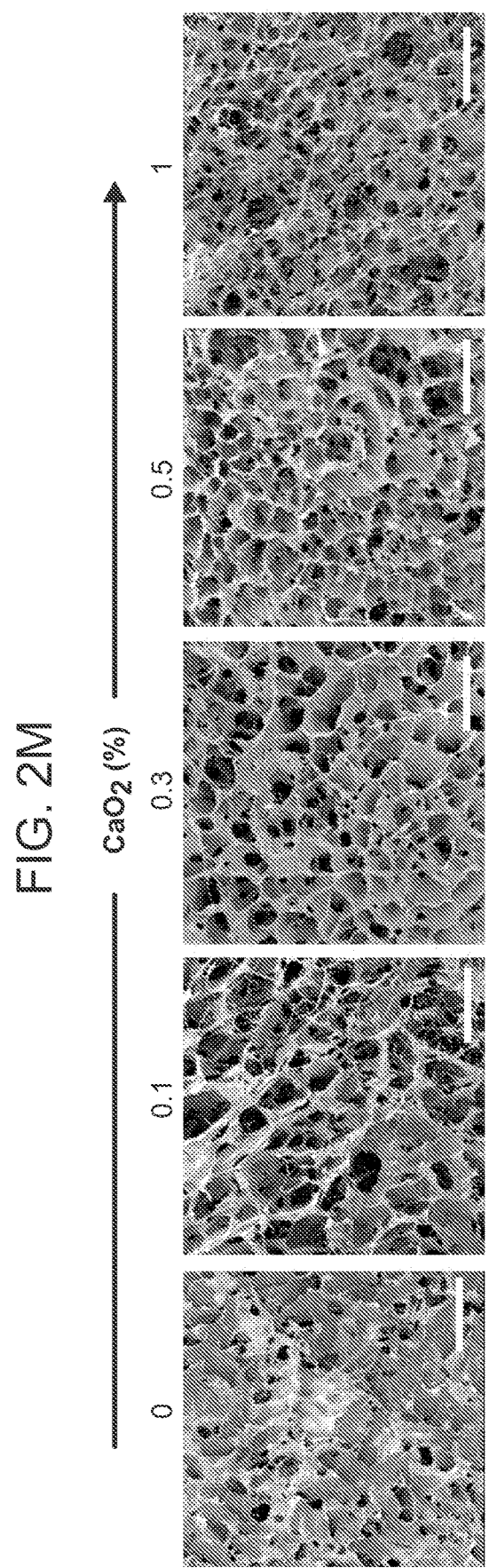

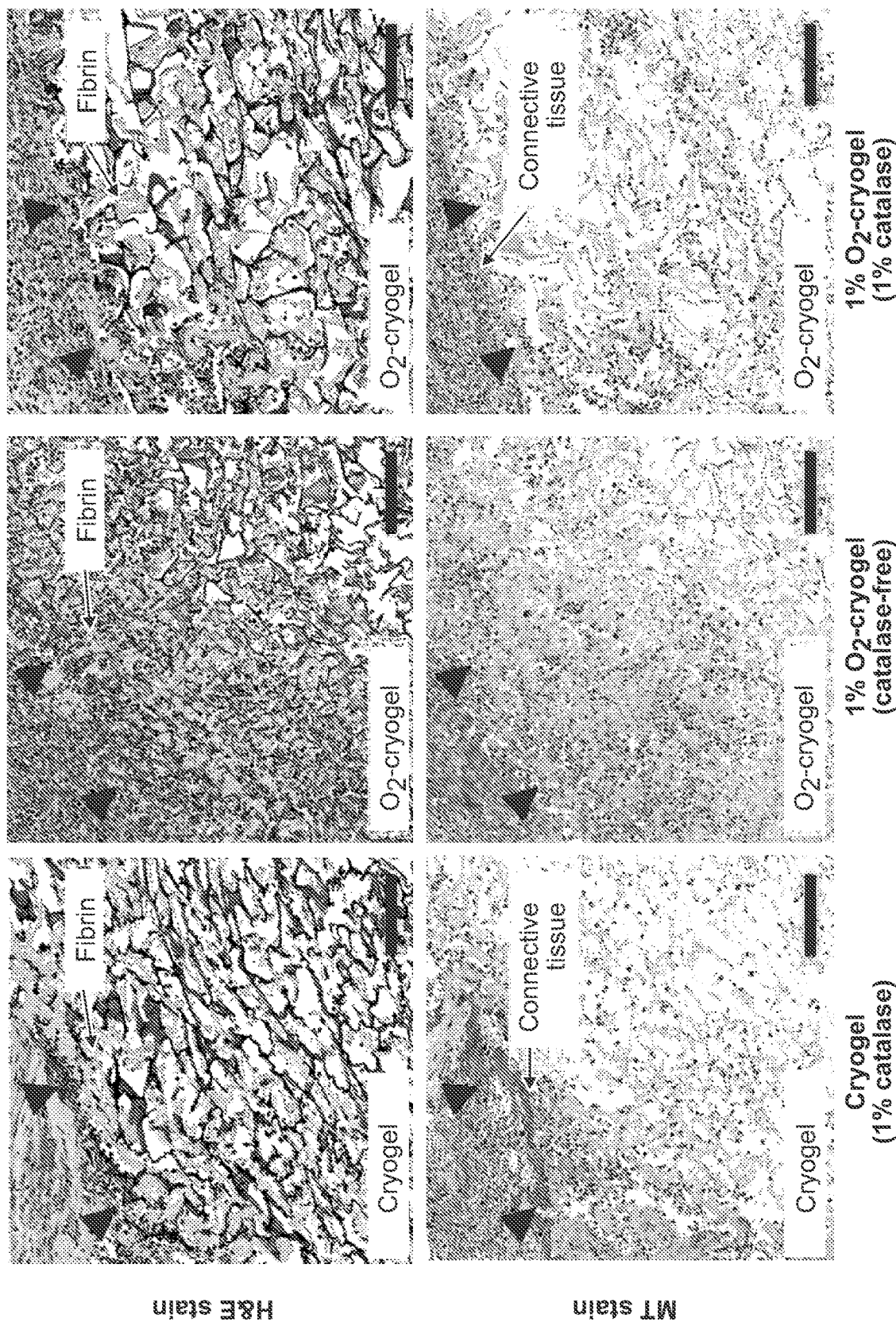

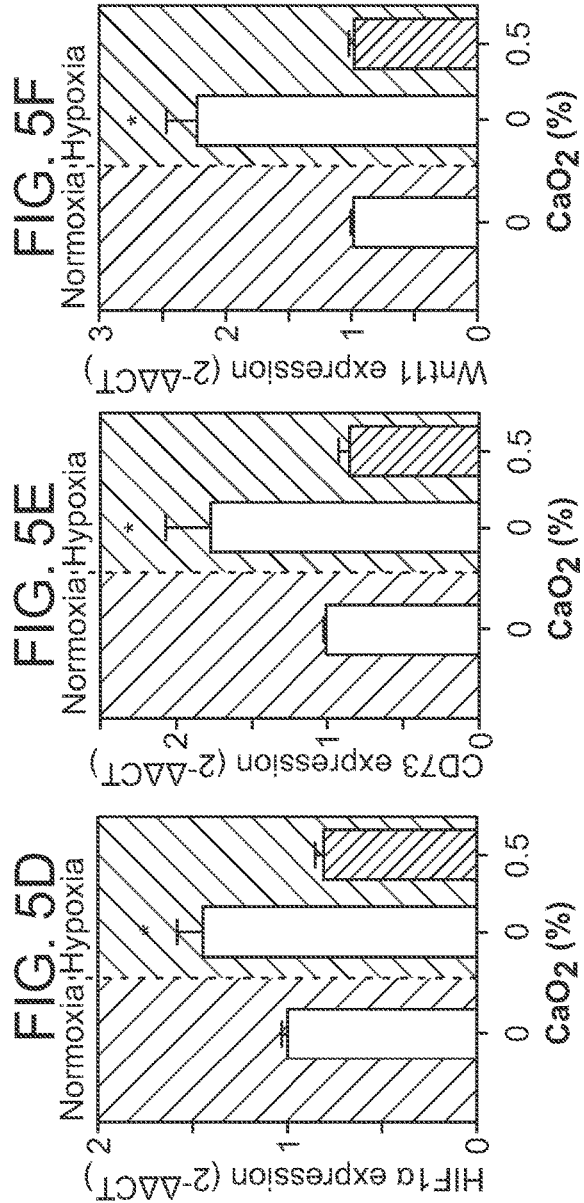
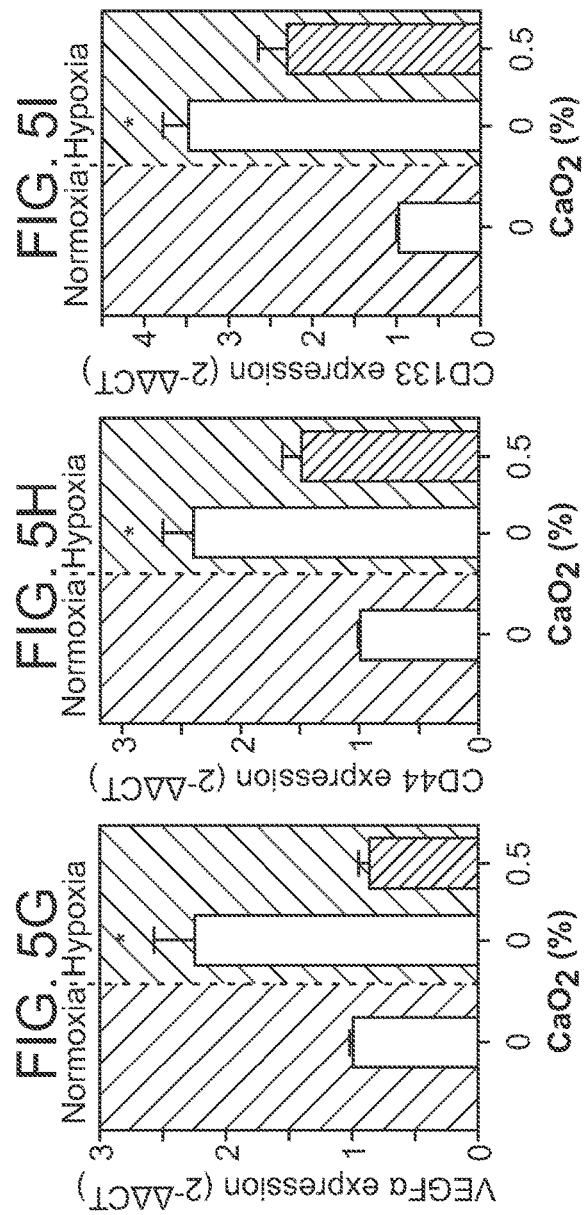

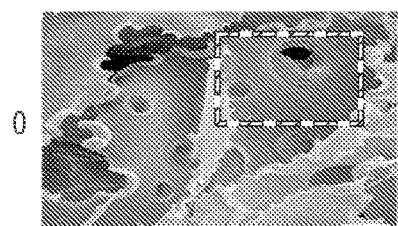
FIG. 7A | FIG. 7B
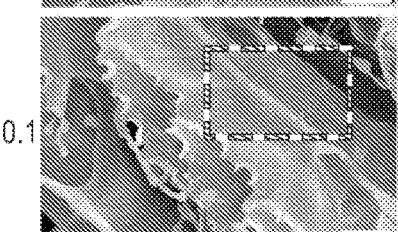
FIG. 7C | FIG. 7D
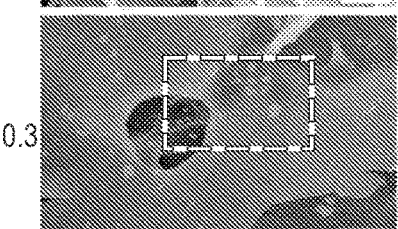
FIG. 7E | FIG. 7F
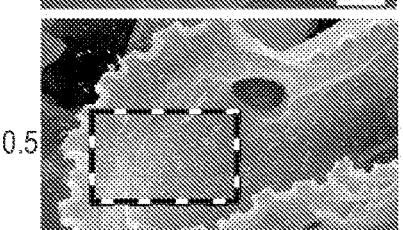
FIG. 7G | FIG. 7H
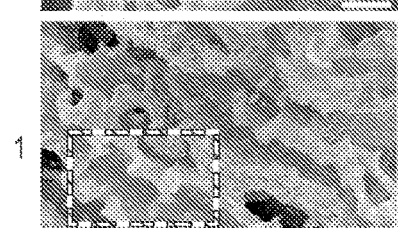
FIG. 7I | FIG. 7J
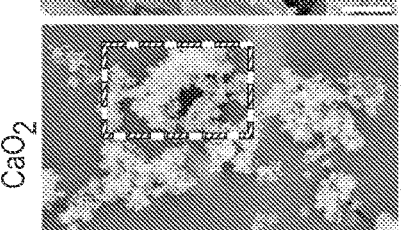
FIG. 7K | FIG. 7L

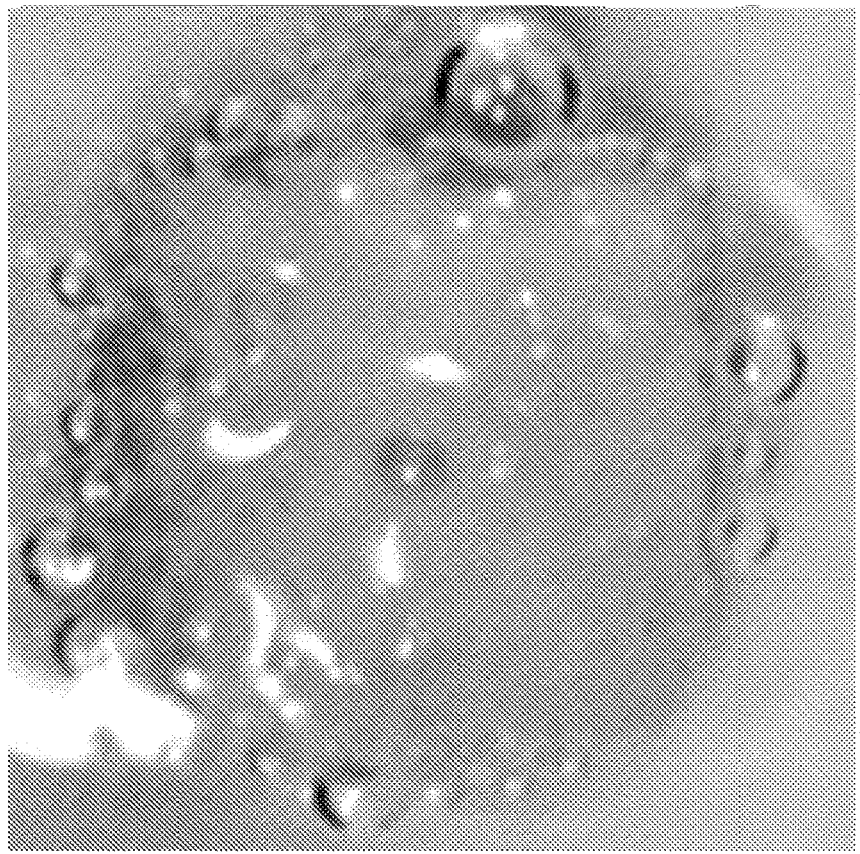
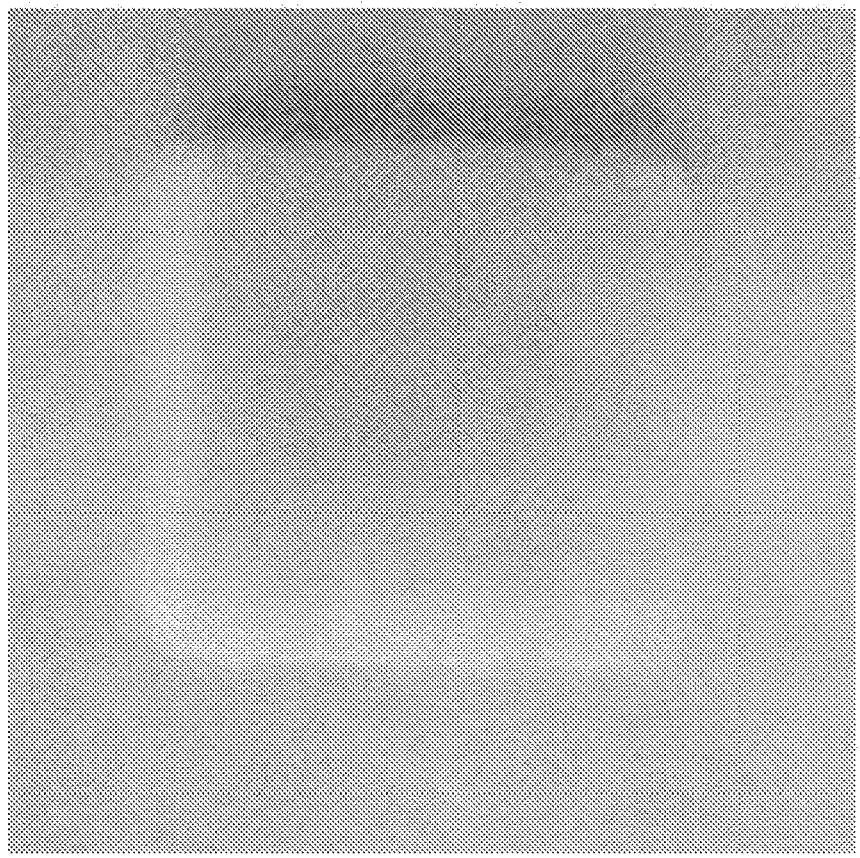
FIG. 9B

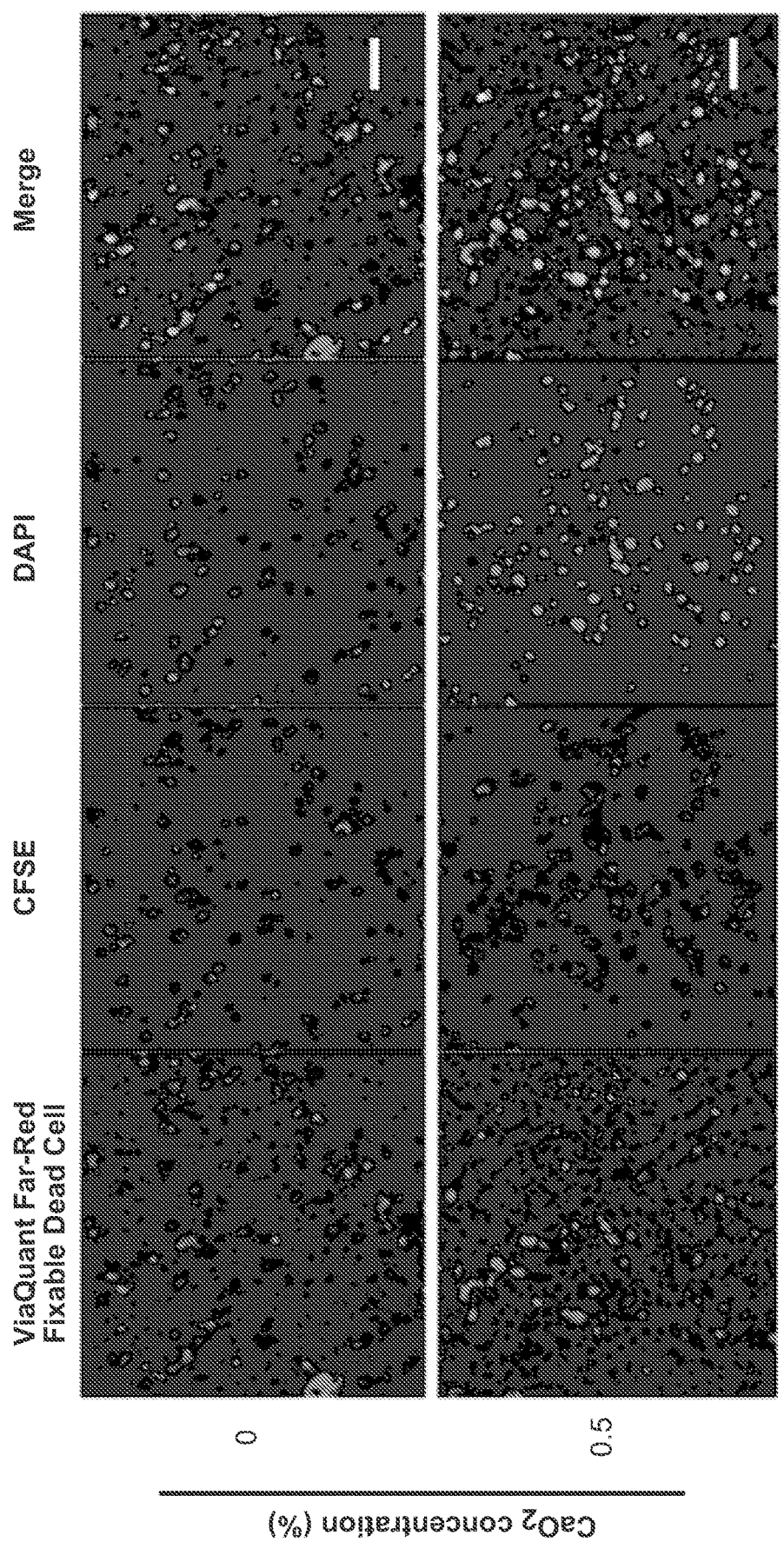

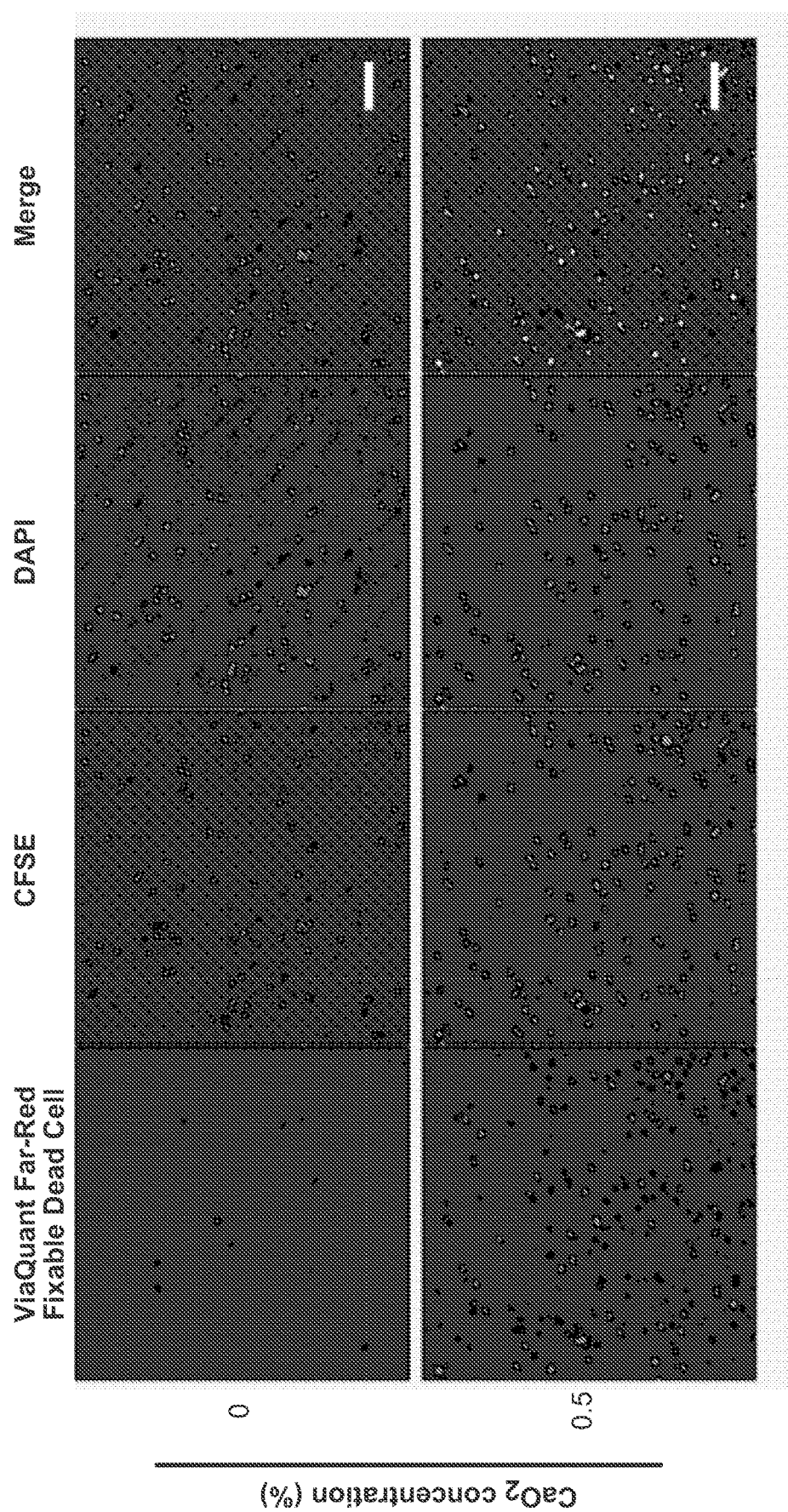

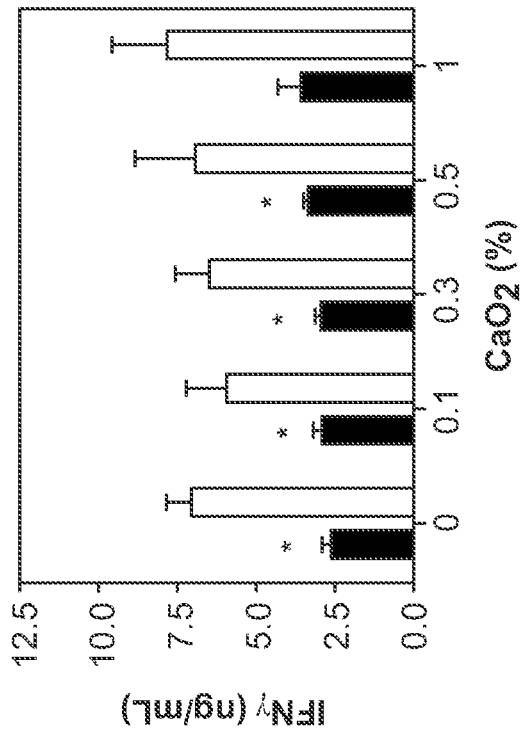
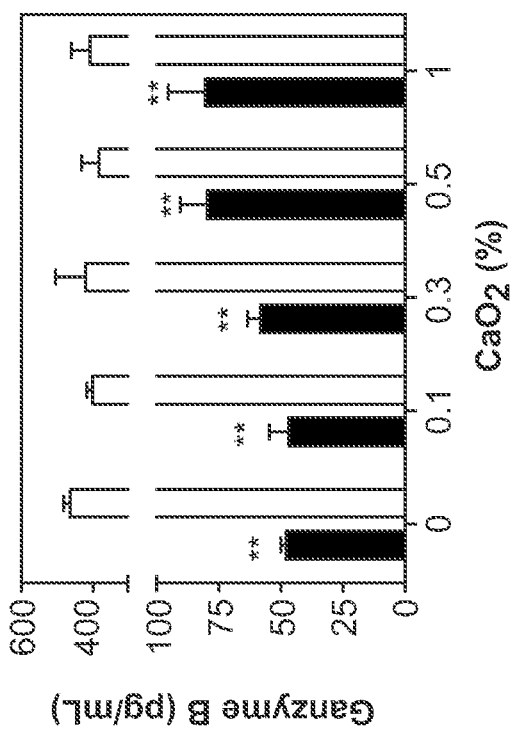
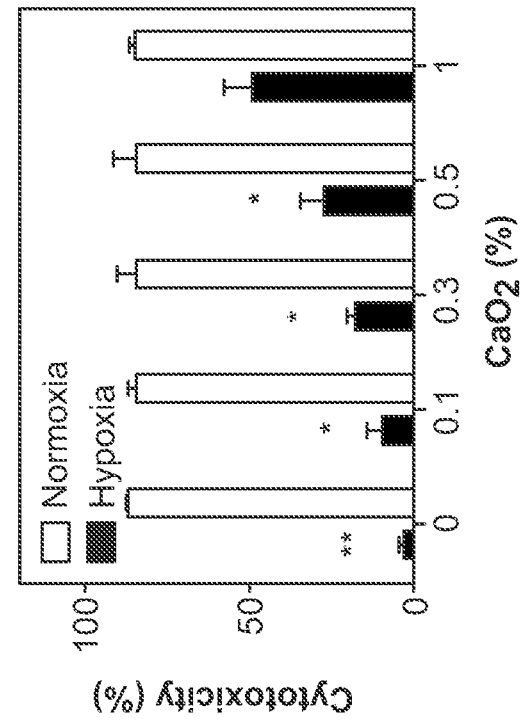
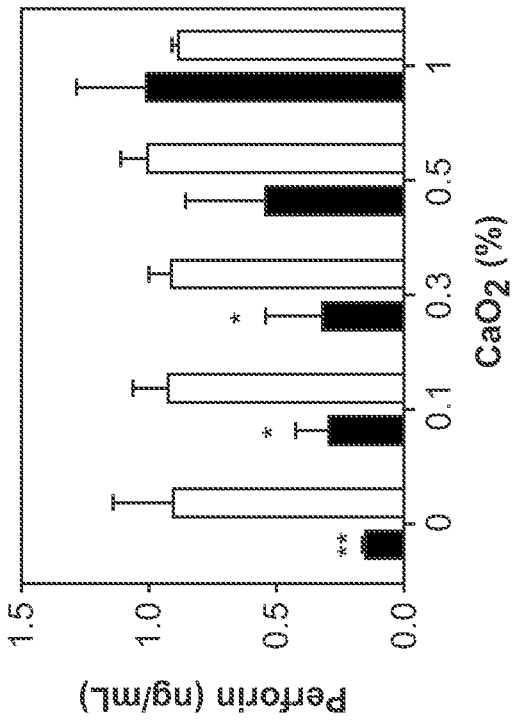

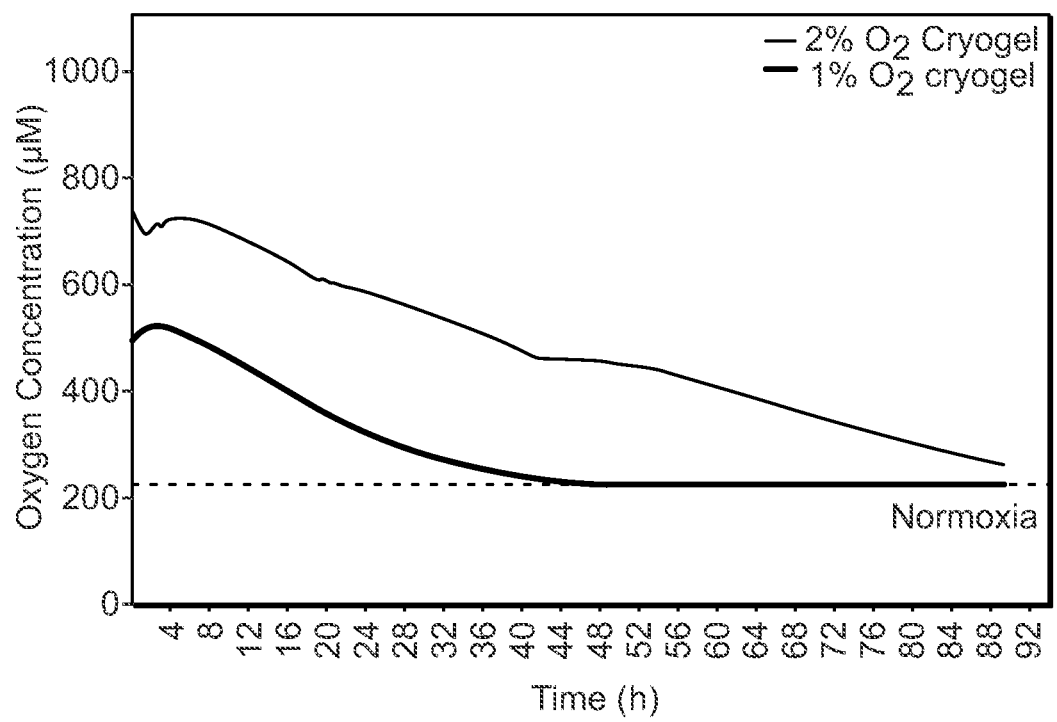

OXYGEN-GENERATING CRYOGELS

RELATED APPLICATIONS

This application is a U.S. National Stage Application of International Application No. PCT/US19/45740, filed Aug. 8, 2019; which claims the benefit of priority to U.S. Provisional Application No. 62/716,132, filed Aug. 8, 2018.

BACKGROUND

Hydrogels have been used for a number of biomedical applications because of their three-dimensional (3D) nature, high water content and the wide range of polymers that can be used for their fabrication. Hydrogels as 3D scaffolds have recently gained momentum because they can mimic key features of the extracellular matrix (ECM), mainly due to their structural similarity with native ECM and their tunable biophysical properties. Recent advances in hydrogel polymerization have led to the development of cryogels, which are highly macroporous hydrogel scaffolds polymerized at sub-zero temperature. These cryogels can have a high level of biocompatibility and display biomechanical properties that recapitulate temporal and spatial complexity of soft native tissues. In addition, cryogels can be functionalized with proteins and/or peptides to enable biological activities (e.g., cell adhesion ligands, antibodies, enzymes), can encapsulate bioactive molecules and control their spatiotemporal release (e.g. cytokines, growth factors), and can be biodegradable (e.g., proteolytic degradability, oxidation, hydrolysis). In addition, cryogels can be delivered in a minimally invasive manner via syringe injection through a conventional small-bore needle or via a catheter. Cryogels can also be introduced into the body via catheter or implanted via surgically. Hydrogels have been described in, for example, U.S. Pat. No. 9,675,561 and US Application Nos. US2019/0076373 and US 2014/0178964, each of which is hereby incorporated by reference in their entirety.

Oxygen ($O_2$) is vital for complex multicellular organisms, both as a signaling molecule or as a regulator of cell metabolism and physiological function. Oxygen is used by cells to produce energy, and as a co-factor or substrate for countless enzymatic reactions. Therefore, oxygen deprivation (defined as hypoxia when the partial pressure of $O_2$ is below 5%) can impact cellular behavior. Hypoxia is encountered in different pathophysiological conditions. For instance, in atherosclerosis and ischemic diseases, hypoxia leads to insufficient cellular function, decrease of nutrient supply and accumulation of toxic metabolic products. In cancer, hypoxia is believed to enable tumor aggressiveness and tumor-induced immunosuppression. Moreover, hypoxia can be responsible for anaerobic bacteria growth in the context of wound healing, or cellular senescence of neo-engineered tissues or organs that lack vascularization.

Cellular responses to hypoxia are induced primarily by the hypoxia-inducible factors (HIFs). HIFs, overexpressed in hypoxic conditions, play a crucial role in adaptive cell responses to oxygen tensions through transcriptional activation of over 100 downstream genes involved in vital biological processes. For instance, HIFs act as key regulators of genes involved in glucose metabolism, cell division, migration, and angiogenesis. HIFs also regulate immune responses. For example, the expression of HIFs can inhibit cytotoxic T cell function while promoting T cell regulatory activity. The latter is triggered by inhibition of type 1 antigen presenting cells (APC), natural killer (NK) cells, and natural killer T (NKT) cells' activity while stimulating myeloid-derived suppressor cell (MDSC) activity. Although hypoxia is an important factor for cancer development and immune system modulation, hypoxia has not been reported to have been reversed locally in a 3D tumor microenvironment, nor are there reports for its implication in biomaterial-based vaccine efficacy.

SUMMARY

Disclosed herein are methods of reducing hypoxia in a biological tissue, comprising administering to the biological tissue an oxygen-generating cryogel (e.g., a macroporous nanocomposite oxygen-generating cryogel); wherein the administration is by injection, catheter, or surgery. In some embodiments, the cryogel comprises a peroxide, an oxide or a percarbonate. In other embodiments, the cryogel releases oxygen for at least about 4 hr, at least about 16 hr, at least about 24 hr, or at least about 48 hr, or at least about 96 hr.

Disclosed herein are methods of treating cancer, comprising administering into a tumor of a mammal an effective amount of an oxygen-generating cryogel (e.g., a macroporous nanocomposite oxygen-generating cryogel); wherein the administration is by injection, catheter or surgery; and the cryogel comprises polymerized hyaluronic acid glycidyl methacrylate, acrylate-PEG-G4RDGSP, acrylate-PEG-Catalase, and $CaO_2$. In some embodiments, the cryogel increases oxygen concentration in the biological tissue to physioxic or normoxic levels. In other embodiments, the tumor is a solid tumor selected from melanoma, renal cell carcinoma, prostate cancer, breast cancer, lung cancer, pancreatic cancer, glioblastoma, ovarian cancer, colon cancer, sarcoma, nasopharyngeal cancer, head and neck cancer, and lymphoma.

BRIEF DESCRIPTION OF THE DRAWINGS

FIG. 2A provides photographs showing cryogels and $O_2$-cryogels before and after syringe injection. Gels were stained with Alizarin Red S. Scale bar: 4 mm.

FIG. 2B depicts a confocal image showing 0% of calcium peroxide ($CaO_2$) particles physically entrapped within the polymer walls.

FIG. 2C depicts a confocal image showing 0.1% of $CaO_2$ particles physically entrapped within the polymer walls.

FIG. 2D depicts a confocal image showing 0.3% of $CaO_2$ particles physically entrapped within the polymer walls.

FIG. 2E depicts a confocal image showing 0.5% of $CaO_2$ particles physically entrapped within the polymer walls.

FIG. 2F depicts a confocal image showing 0.5% of $CaO_2$ particles physically entrapped within the polymer walls.

FIG. 2G depicts a confocal image showing 1% of $CaO_2$ particles physically entrapped within the polymer walls.

FIG. 2H is a SEM image depicting $CaO_2$-free cryogels. Pseudo-coloring in pink was used to highlight $CaO_2$ nanoparticles.

FIG. 2I is a SEM image depicting $CaO_2$ entrapped within the polymer walls of 0.5% $O_2$-cryogels. Pseudo-coloring in pink was used to highlight $CaO_2$ nanoparticles.

FIG. 2M is a SEM image depicting the pore size of $O_2$-cryogels.

FIG. 2P is a bar graph depicting the Young's moduli of $O_2$-cryogels.

FIG. 3A depicts $H_2O_2$ release from catalase-free (white) and (red, catalase-containing) $O_2$-cryogels.

FIG. 3B is a scheme depicting the oxygen-measurement setup.

FIG. 3C depicts controlled release of oxygen from cryogels and $O_2$-cryogels in normoxic condition.

FIG. 3D depicts controlled release of oxygen from cryogels and $O_2$-cryogels in hypoxic condition.

FIG. 3E-FIG. H depict controlled release of oxygen from various percentage of $O_2$-cryogels before (green) and after (orange) mechanical compaction in normoxic conditions.

FIG. 3E shows oxygen release after 0.1% compaction.

FIG. 4A-FIG. 4D depict $O_2$-cryogel cytocompatibility (in vitro) and biocompatibility (in vivo)

FIG. 4A is a bar graph depicting B16-F10 melanoma cell viability after 24 hr incubation within cryogels and $O_2$-cryogels in normoxic (20% $O_2$) conditions.

FIG. 4B is a bar graph depicting B16-F10 melanoma cell viability after 24 hr incubation within cryogels and $O_2$-cryogels in hypoxic (1% $O_2$) conditions.

FIG. 4C provides confocal images of B16-F10 melanoma cell viability after 24 hr incubation within cryogels and $O_2$-cryogels in normoxic (top images) and hypoxic (bottom images) conditions. Blue=nuclei stained with DAPI, red=dead cells stained with ViaQuant Far Red, green=actin cytoskeleton stained with alexa fluor 488 phalloidin, yellow=polymer walls stained with rhodamine.

FIG. 4D depicts histological analysis (H&E stain and MT stain) of explanted cryogels (containing 1% catalase), 1% $O_2$-cryogels (containing 1% catalase), and 1% $O_2$-cryogels (catalase-free) at day 7 post subcutaneous injection. Arrows indicate the border between cryogels/$O_2$-cryogels and the host tissue.

FIG. 5A-FIG. 5D depict $O_2$-cryogel-mediated reoxygenation reverses cellular tumor hypoxia.

FIG. 5A depicts hypoxia detection assay of B16-F10 melanoma cells cultured in 1% $O_2$ for 24 hr in cryogels and $O_2$-cryogels. Blue=nuclei stained with DAPI, green=hypoxic cells stained with hypoxyprobe.

FIG. 5B is a bar graph depicting quantification of cellular hypoxia following a 24 hr incubation period in cryogels and $O_2$-cryogels in normoxic (red background; left) or hypoxic (blue background; right) conditions.

FIG. 5C is a bar graph depicting adenosine concentration in B16-F10 melanoma cell supernatant after 24 hr incubation in cryogels and $O_2$-cryogels in normoxic (red background; left) and hypoxic (blue background; right) conditions.

FIG. 5D-FIG. 5I are bar graphs depicting HIF1α (FIG. 5D), Wnt11 (FIG. 5E), CD73 (FIG. 5F), VEGFα (FIG. 5G), CD44 (FIG. 5H) and CD133 (FIG. 5I) expression levels in B16-F10 melanoma cells after 24 hr incubation in cryogels and 0.5% $O_2$-cryogels in normoxic (red background; left) and hypoxic (blue background; right) conditions.

FIG. 6A is a scheme depicting restored T-cell activity in $O_2$-cryogels.

FIG. 6B are time-lapse images showing OT-1 T cells attacking B16-ova cells after 1 hr (top) and 4 hr (bottom) incubation under hypoxic (1% $O_2$) conditions in cryogels and 0.5% $O_2$-cryogels. Tumor cells and OT-1 T cells are pseudo-colored in green and red, respectively.

FIG. 6C are confocal images B16-ova cells co-cultured with OT-1 T cells for 24 hr in hypoxic (1% $O_2$, blue background) condition. Red=dead cells stained with ViaQuant Far Red, blue=nuclei stained with DAPI.

FIG. 6D is a bar graph depicting quantification of T cell-mediated cytotoxicity.

FIG. 6E is a bar graph depicting secretion of IFNγ from OT-1 T cells.

FIG. 6F is a bar graph depicting secretion of granzyme B from OT-1 T cells.

FIG. 6G is a bar graph depicting secretion of perforin (g) from OT-1 T cells.

FIG. 7A-FIG. 7I are SEM images of entrapped $CaO_2$ within polymer walls of $O_2$-cryogels.

FIG. 7A and FIG. 7B representative SEM images (n=5) showing 0% of $CaO_2$ particles (control) within the polymer walls. Scale bars: 50 μm (FIGs. A, C, E, G, I), 25 m (FIGs. B, D, F, H, J), 10 μm (FIG. K), and 5 μm (FIG. 1).

FIG. 7C and FIG. 7D are representative images (n=5) showing 0.1% of $CaO_2$ particles within the polymer walls.

FIG. 7E and FIG. 7F are representative images (n=5) showing 0.3% of $CaO_2$ particles within the polymer walls.

FIG. 7G and FIG. 7H are representative images (n=5) showing 0.5% of $CaO_2$ particles within the polymer walls.

FIG. 7I and FIG. 7J are representative images (n=5) showing 1% of $CaO_2$ particles within the polymer walls.

FIG. 7K and FIG. 7L representative images (n=5) showing free $CaO_2$ nanoparticles (control) within the polymer walls.

FIG. 9A-FIG. 9C shows how catalase induces controlled $H_2O_2$ depletion and rapid oxygen release.

FIG. 9A a bar graph depicting enzymatic activity of catalase (non-conjugated) and ACRL-PEG-Catalase in 50 μM $H_2O_2$.

FIG. 9B are photographs of catalase-free (left) and 1% wt/v catalase-containing cryogels (right, active oxygen release produces bubbles) immersed in a solution of 50 mM $H_2O_2$ for 5s.

FIG. 9C is a photograph depicting the experimental setup.

FIG. 10A-FIG. 10B depict the cytotoxic activity of OT-1 T cells cultured in B16-ova cell-laden $O_2$-cryogels.

FIG. 10A are confocal images depicting B16-ova cell viability within $O_2$-cryogels after 24 hr incubation with OT-1 T cells in normoxic (20% $O_2$) condition. Red=dead cells stained with ViaQuant Far Red, blue=nuclei stained with DAPI, green=B16-ova cells stained with CFSE. Scale bar=50 μm (a) and 100 μm (b).

FIG. 10B are confocal images depicting B16-ova cell viability within $O_2$-cryogels after 24 hr incubation with OT-1 T cells in hypoxic (1% $O_2$) conditions. Red=dead cells stained with ViaQuant Far Red, blue=nuclei stained with DAPI, green=B16-ova cells stained with CFSE. Scale bar=50 μm (a) and 100 μm (b).

FIG. 11A-FIG. 11D depict rescuing cytotoxic T-cell activity against tumor cells with $O_2$-cryogels.

FIG. 11A is a bar graph depicting quantification of T cell-mediated cytotoxicity against B16-ova cells after B16-ova cells were co-cultured with OT-1 T cells for 4 hr in normoxic (20% $O_2$, red) or hypoxic (1% $O_2$, blue) conditions.

FIG. 11B is a bar graph depicting secretion of IFNγ after B16-ova cells were co-cultured with OT-1 T cells for 4 hr in normoxic (20% $O_2$, red) or hypoxic (1% $O_2$, blue) conditions.

FIG. 11C is a bar graph depicting secretion of perforin after B16-ova cells were co-cultured with OT-1 T cells for 4 hr in normoxic (20% $O_2$, red) or hypoxic (1% $O_2$, blue) conditions.

FIG. 11D is a bar graph depicting secretion of granzyme after B16-ova cells were co-cultured with OT-1 T cells for 4 hr in normoxic (20% $O_2$, red) or hypoxic (1% $O_2$, blue) conditions.

FIG. 12A shows $CD11c^{High}$ $CD86^{High}$ cell markers.
FIG. 12B shows $CD11c^{High}$ $MHCII^{High}$ cell markers.
FIG. 12C shows $CD11c^{High}$ $CD317^{High}$ cell markers.
FIG. 12D shows IL-12p70 secretion from BMDC cells.
FIG. 12E shows IL-6 secretion from BMDC cells.
FIG. 12F shows TNFα secretion from BMDC cells.

FIG. 13 depicts controlled release of oxygen from $O_2$-cryogels containing 1% or 2% $CaO_2$ (wt/v) under normoxic conditions.

DETAILED DESCRIPTION

Figure 1A:
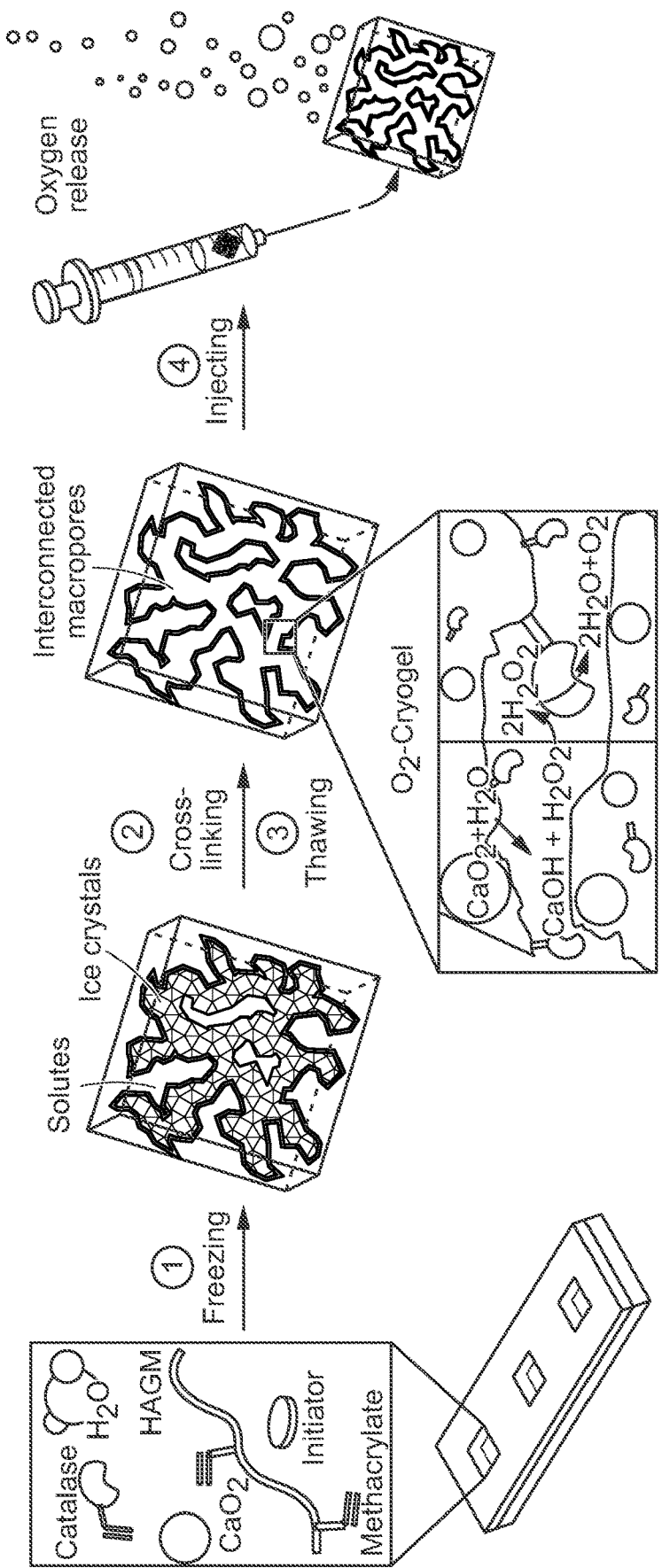
FIG. 1A is a scheme depicting the fabrication process of $O_2$-cryogels.
Figure 1B:
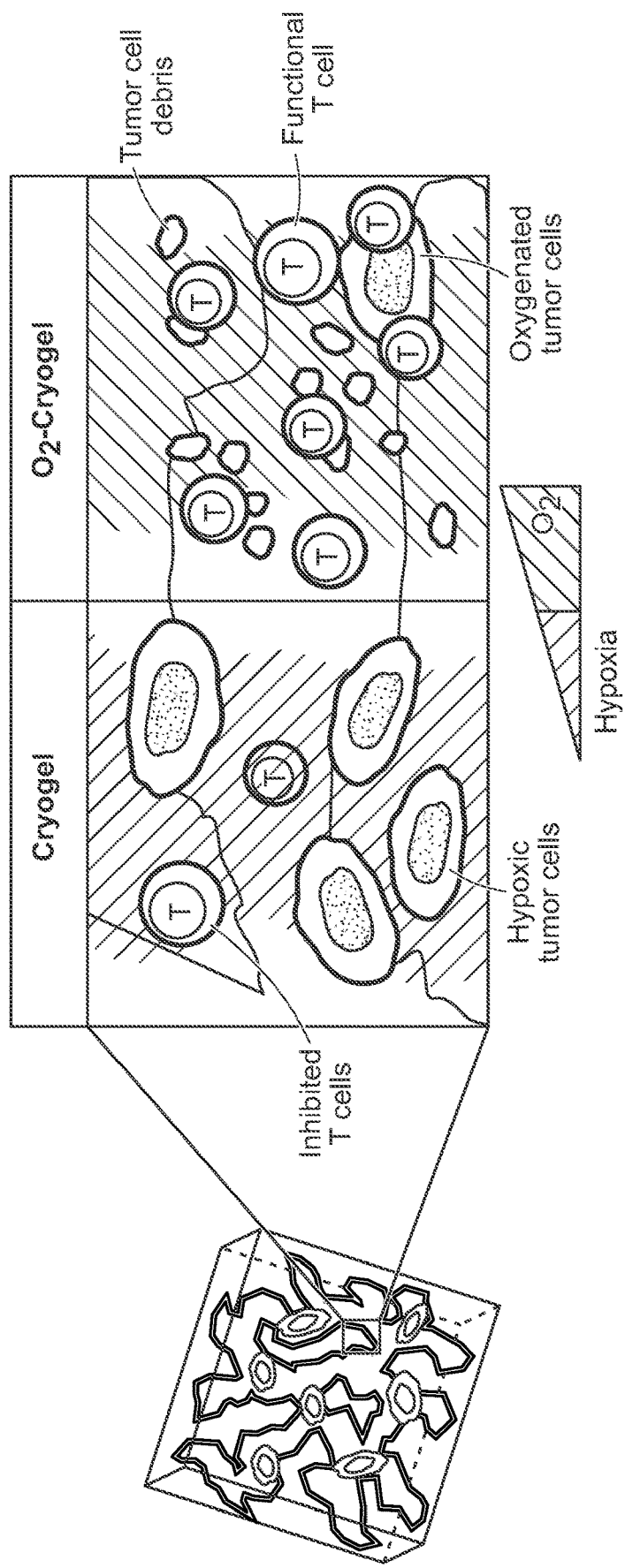
FIG. 1B depicts $O_2$-cryogels' ability to rescue T cell-mediated cytotoxicity in a hypoxic tumor microenvironment.

Cancerous tissue hypoxia and hypoxia-inducible factor 1alpha (HIF1α) represent a driving force for tumor cell growth, invasion, aggressiveness and creation of an immunosuppressive tumor microenvironment (TME). Targeting hypoxia-induced immunosuppression is a promising strategy to prevent immune escape and overcome resistance to cancer therapies. A safely injectable biomaterial system capable of producing oxygen and reversing local cancerous tissue hypoxia by increasing local oxygen tension has the potential to improve the infiltration and rescue effector functions of the otherwise hypoxia-HIF1α inhibited anti-tumor T cells, thereby enabling the full therapeutic capacities of current cancer immunotherapies.

Provided herein is an injectable oxygen-generating biomaterial capable of rapidly and efficiently reversing local hypoxia while reactivating immunosuppressed cytotoxic T cell activity. These oxygen-generating cryogels ($O_2$-cryogels) were engineered to release high, sustained concentrations of oxygen while retaining the unique and advantageous features of cryogels, including an interconnected macroporous network, mechanical robustness, as well as syringe injectability and shape-memory properties. $O_2$-cryogels demonstrated high cell cytocompatibility and biocompatibility in mice, as well as a controlled release of oxygen allowing for the rapid reversal of local hypoxia. This resulted in the inhibition of hypoxia-inducible gene expression by hypoxic cells and the downregulation of immunosuppressive extracellular adenosine accumulation associated with hypoxic tumors. $O_2$-cryogels restored the lethal antigen-specific cytotoxicity of previously hypoxic T cells against tumor cells within a few hours.

An investigation of the underlying mechanisms indicated that $O_2$-cryogels did suppress hypoxia-induced T cell immunosuppression by i) promoting T cell-tumor cell interactions as evidenced by time-lapse imaging, ii) increasing the secretion of cytotoxic proteins towards tumor cells, including perforin and granzyme B and, as a results, iii) rescuing the ability of antigen-specific T cells to deliver the lethal hit leading to the tumor cell lysis and death. Taken together, these findings clearly support the notion that $O_2$-cryogels represent an attractive class of biomaterials for cancer research and therapies since it was capable of reversing hypoxia-induced immunosuppression and re-activating T cell anti-tumor activity. This platform has the potential to better understand the interplay between immune and tumor cells, deliver oxygen as an immunological co-adjuvant, and to improve existing or under investigation cancer immunotherapies.

Despite recent advances in cancer therapies, the tumor microenvironment (TME) engenders various obstacles that hinder tumor eradication. Many forms of immunotherapy have been designed to overcome these challenges, including blockers of hypoxia-adenosinergic immunosuppression and blockers of immunological negative regulators PD-1 and CTLA-4. They are capable of reprogramming the patient's own immune system to recognize and eliminate tumor cells while creating a memory response to prevent tumor recurrence. However, generating sustained and durable clinical responses remains challenging. It has recently come to light that the limited success of many cancer therapies could be attributed to tumor-protecting mechanisms that allow for immune evasion in a hostile, immunosuppressive TME. Therefore, the development of strategies to reverse tumor-induced immunosuppression has been an intense focus of cancer research to achieve maximal therapeutic efficacy in many cancer treatments.

Hypoxia, an established feature of solid tumors, has been associated with poor clinical outcome for patients suffering from various tumor types. Hypoxic tumors respond poorly to systemic therapies and radiotherapy, are resistant to apoptosis, and possess a more aggressive phenotype leading to local invasion and metastasis. Furthermore, hypoxia also induces a local immunosuppressive environment. Hypoxia-adenosinergic immunosuppression was first identified as a powerful mechanism that protects inflamed normal tissues from excessive collateral damage by anti-pathogen immune cells, and then as the protector of cancerous tissues from anti-tumor T cells. These immunosuppressive effects of hypoxia are primarily mediated by A2A adenosine receptors (A2ARs) and hypoxia-inducible factors (HIFs).

Tumor-hypoxia is associated with the accumulation of extracellular adenosine via the adenosine-generating ecto-enzymes CD39 and CD73, that signal through cAMP-elevating A2ARs on the surface of immune cells. Adenosine signaling has been shown to suppress the anti-tumor activity of T-cells and NK cells, particularly in terms of cytotoxic effector functions and secretion of important proinflammatory cytokines (e.g., IFNγ). Several classes of therapeutics that reverse hypoxia-induced immunosuppression to prevent the inhibition of anti-tumor immunity have been investigated, including hypoxia-activated prodrugs, gene therapy, bacterial therapy, A2AR antagonists, HIF inhibitors, and supplemental oxygenation therapy. Recent clinical studies using antagonists of A2AR have shown the great promise of targeting of the hypoxia-adenosinergic pathway in cancer immunotherapy. Similarly, preclinical studies have demonstrated the power of using oxygenating agents to enhance anti-tumor immunity and induce tumor regression. Therefore, there is an increasing interest in developing more potent and specific strategies to reverse tumor hypoxia-driven immunosuppression and create an immunopermissive TME that can dramatically improve cancer therapy.

Among the therapeutic options under investigation for cancer patients, reversing hypoxia-induced immunosuppression has recently become a very attractive strategy. Patients with hypoxic tumors have poor clinical outcomes. Tumor hypoxia is typically associated with the most aggressive forms of the disease leading to therapeutic resistance to radiotherapy, chemotherapy and immunotherapy. Recently, strategies targeting tumor hypoxia (e.g., hypoxia-activated prodrugs, oxygenation therapy) or hypoxia-inducible signaling pathways (e.g., HIF inhibitors, A2AR antagonists) have shown potential efficacy in preclinical and clinical studies. These approaches can boost tumor-specific cytotoxic T cell and NK cells, thereby facilitating tumor clearance. However, to date, hypoxia-targeted therapy is still not adopted as a standard treatment due to the low efficacy and significant toxicity of currently available approaches. Therefore, there is a crucial need to develop new strategies for reversing tumor hypoxia. Disclosed herein is an approach by using oxygen-generating biomaterials, such as cryogels.

An oxygen-generating biomaterial capable of reversing an immunosuppressive hypoxic TME, can reactivate inhibited T cell function and activity, and ultimately reinforce T-cell mediated killing of tumor cells. Recent advances from tissue engineering and regenerative medicine have demonstrated that incorporation of peroxides and percarbonate particles or hydrogen peroxide ($H_2O_2$) in biomaterials allows for the efficient production of oxygen. These biomaterials gradually release oxygen in a spatiotemporally controlled manner when exposed to water and are typically coupled with an antioxidant agent to attenuate toxic free radical byproducts. Biomaterials can also function as in vivo drug delivery systems that increase the efficacy of immunotherapeutic agents by enhancing their stability, localization, kinetics of release, and biodistribution. However, biomaterials often require an invasive procedure to be administered in the body, thereby limiting their utility. Moreover, although highly interconnected macroporous structures are necessary to facilitate oxygen diffusion, fabrication of macroporous biomaterials remains challenging due to their weak mechanical properties, lack of pore interconnectivity or potential cytotoxicity.

Disclosed herein is a new class of biomaterial scaffolds that is able to generate oxygen in a controlled and sustained manner, allowing for the reversal of local hypoxia and restoration of the cytotoxic activity of tumor-specific T cells. These oxygen-generating cryogels were fabricated by trapping solid $CaO_2$ particles within the polymer network during a one-step cryopolymerization. In addition, to prevent hydrogen peroxide-derived toxicity, chemically modified catalase was grafted into the $O_2$-cryogels during cryogel synthesis. Ultimately, $CaO_2$ particles were homogenously distributed throughout the cryogel structure, providing predictable and spatiotemporally controllable oxygen production and release.

Provided herein are injectable macroporous oxygen-generating cryogels ($O_2$-cryogels) capable of re-oxygenating the tumor microenvironment, reversing hypoxia-driven immunosuppression, and ultimately restoring anti-tumor cytotoxic T cell activity. To mimic the TME, a naturally occurring glycosaminoglycan (Hyaluronic acid, HA) that serves as a major component of the tumor extracellular matrix (ECM) was used to fabricate cryogel scaffolds. Furthermore, these three-dimensional (3D) scaffolds were hybridized with calcium peroxide ($CaO_2$) particles and conjugated with catalase (CAT) to locally boost oxygen release while minimizing cytotoxicity. The physical properties of $O_2$-cryogels include their unique interconnected macroporous network, shape memory properties, syringe injectability, and ability to be administered by catheter. $O_2$-Cryogels are able to release oxygen in a controlled and sustained fashion, both in normoxic and hypoxic conditions, while being inherently cytocompatible and biocompatible. They have the potential to reverse tumor cell hypoxia, downregulate the expression level of hypoxia-induced proteins, and reduce the accumulation of immunosuppressive extracellular adenosine. $O_2$-Cryogels can reactivate inhibited T cells and restore their anti-tumor activity tested in an in vitro OT-I melanoma mouse model.

Disclosed herein is an oxygen-generating biomaterial that can be used as i) a strategy to reverse tumor-associated hypoxia and ii) and approach to better understand the effect of local oxygenation on T cell function and activity. Suitable hydrogels have been described in, for example, U.S. Pat. No. 9,675,561 and US Application Nos. US2019/0076373 and US 2014/0178964, each of which is hereby incorporated by reference in their entirety.

The present invention addresses the need for fundamental technology and materials that can serve as oxygenated 3D microenvironments to study the impact of hypoxia and its suppression on tumor development and progression, on immune cell function and activity, and ultimately, on immune responses. Provided herein are methods to reverse hypoxia-induced immunosuppression that can be used in-vivo as a co-adjuvant therapy or as a system to improve cancer immunotherapy.

Disclosed herein is a minimally-invasive strategy to administer macroporous nanocomposite biodegradable cryogels as a 3-D platform. Cryogel size can vary from [fill in] to less than 1 mm. Any biocompatible polymers or monomers undergoing cryopolymerization can be utilized. Suitable polymers and monomers include, but are not limited to, naturally derived polymers (alginate, hyaluronic acid, chitosan, heparin, cellulose ethers (e.g. carboxymethyl cellulose, cellulose), elastin, gelatin, starch, carob gum, pectin, guar gum, carrageenan collagen, xanthan gum, fibronectin, elastin, albumin, lignin, glycosaminoglycans, chitin (including nanofibril form) etc.) and synthetic polymers (poly(ethylene glycol) (PEG), PEG-derivatives such as PEG-co-poly(glycolic acid; PGA) and PEG-co-poly(L-lactide; PLA), poly(2-hydroxyethyl methacrylate) (pHEMA), poly-2-hydroxyethylacrylate (polyHEA), PAAm, poly(N-isopropylacrylamide) (PNIPAAm), polyamines and polyethyleneimines, polyvinyl alcohol, polyacrylamides, polyacrylic acid, polymethacrylic acid, poly(glycerol) sebacate, poly(serinol sebacate), etc.)

The strategies described herein are for minimally invasive delivery of preformed nanocomposite biomaterials. Injectable nanocomposite biomaterials are useful as surgical tissue adhesives, space-filling injectable materials for hard and soft tissue repair, drug delivery, and tissue engineering.

In addition to the free radical polymerization process to cross-link the polymers and make chemically cross-linked injectable cryogels (polymerization time is about 17 hr), gels are optionally polymerized using other processes. Injectable cryogels can be classified under two main groups according to the nature if their cross-linking mechanism, namely chemically and physically cross-linked gels. Covalent cross-linking processes include radical polymerization (vinyl monomers reaction), Michael-type addition reaction (vinyl-thiol reaction), polycondensation (esterification reaction between alcohols and carboxylic acids or amide formation between carboxylic acids and amines), oxidation (thiol-thiol cross-linking), click chemistry (1,3-dipolar cycloaddition of organic azides and alkynes), Diels-Alder reaction (cycloaddition of dienes and dienophiles), Oxime, Imine and Hydrazone chemistries. Non-covalent cross-linking include ionic cross-linking (e.g., alginate crosslinking with calcium, magnesium, potassium, barium), self-assembly (phase transition in response to external stimuli, such as temperature, pH, ion concentration, hydrophobic interactions, protein-protein interactions, light, metabolite, and electric current).

In some embodiments, the cryogel comprises molecular oxygen. In addition to calcium peroxide, sodium percarbonate $((Na_2CO_3)_2 \cdot 1.5H_2O_2)$, magnesium peroxide $(MgO_2)$ and encapsulated $H_2O_2$/Polyvinylpyrrolidone (PVP) can be utilized as oxygen generating species. In addition to calcium peroxide, all peroxides (e.g., magnesium peroxide, hydrogen peroxide), oxides (e.g., manganese dioxide, zinc oxide) and percarbonates (e.g., sodium percarbonate) can be utilized as oxygen-generating species. Polymer (e.g. PLA, PGA, PLGA, PCL, PDMS, PVP) coating or encapsulation of oxygen generating species can be performed to extend and tune the oxygen release period.

In addition to releasing oxygen, cryogels are optionally loaded with therapeutic checkpoint inhibitors to reverse hypoxia-driven immunosuppression and restore effective and long-lasting immune responses. For example, adenosine receptor antagonists (all the molecule antagonists for A2a, A2b or A3 receptors) can be encapsulated within cryogels or $O_2$-cryogels and then released in a controlled and sustained fashion. Specific examples of adenosine receptor antagonists, include, but are not limited to: ZM241385; 1,7-methylxantine (caffeine); theophylline; theobromine; SCH 58261 [7-(2-phenylethyl)-5-amino-2-(2-furyl)-pyrazolo-[4,3-e]-1,2,4-triazolo[1,5-c]pyrimidine](Schering-Plough Research Institute, Milan, Italy); and KW-6002 [(E)-1,3-diethyl-8-(3,4-dimethoxystyryl)-7-methyl-3,7-dihydro-1H-purine-2,6-dione]. Examples of antagonists are described in U.S. Pat. Nos. 5,565,566; 5, 545, 627, 5,981,524; 5,861,405; 6,066,642; 6,326,390; 5,670,501; 6,117,998; 6,232,297; 5,786,360; 5,424,297; 6,313,131, 5,504,090; and 6,322,771 (all of which are incorporated by reference). Immune checkpoint inhibitors could either be physically entrapped or covalently conjugated to the cryogels.

Further additional agents that can be incorporated into the present cryogels include cytokines, adjuvants, and tumor-associated antigens (cells, proteins, tumor lysates) that are useful in $O_2$-cryogel based vaccines.

The oxygen production by $O_2$-cryogels was sufficiently high with a maximum of 800 μM of dissolved oxygen after 2 hr, sustained up to 4 days, and tunable by varying the concentration of $CaO_2$. In some embodiments, $O_2$-cryogels reversed hypoxia in less than 10 min ($O_2$ concentration >5%), and reached physioxia ($O_2$ concentration=8%) in 30 min.

Moreover, while the diffusion of oxygen can be very limited in conventional nanoporous gels, the macroporous network generated by cryopolymerization appears to be essential for optimal oxygenation with total cellular hypoxia reversion throughout the full scaffolds for at least 24 hr. Indeed, hypoxia is modulated by oxygen release into the surrounding environment, which efficiently and quickly restored oxygen tension. However, oxygen release is expected to be slower and more sustained in vivo due to the artificial nature of in vitro release studies as cryogels are subjected to environments with increased water content. The current oxygen generation profile is based on (i) the free diffusion of water across the polymer network, a step necessary to hydrolyze entrapped $CaO_2$ particles, (ii) kinetics of oxygen production, and (iii) oxygen release rate.

Ultimately, oxygen-generating scaffolds could be used to prevent hypoxia-mediated cell death. $O_2$-cryogels possess a highly interconnected macroporous structure and swelling ratio which makes them suitable for cell infiltration and proliferation, nutrient diffusion, as well as waste removal. In addition, these injectable scaffolds also exhibit soft tissue-like Young's moduli that matches biomechanical features of native soft tissues. Furthermore, to prevent anoikis and enhance cell-scaffold interaction, G4RGDSP adhesion peptides were conjugated to $O_2$-cryogels. Moreover, chemically modified catalase was also grafted to cryogels to deplete effectively $H_2O_2$ and boost oxygen generation. As a result, $O_2$-cryogels show high biocompatibility following injection in mice independently of $CaO_2$ concentration, and cells cultured within these scaffolds remained viable, both in normoxic and hypoxic conditions.

In the context of cancer immunotherapy, oxygen-generating biomaterials could reactivate inhibited tumor-reactive T cells when exposed to hypoxia. Such biomaterials could be combined with other strategies under development for disrupting hypoxia-driven T cell immunosuppression, including A2AR antagonists, HIFs inhibitors, and oxygen therapy. Combination therapies exploit the chances for a synergistic anti-tumor effect. $O_2$-cryogels are able to restore T cell-mediated anti-tumor activity in hypoxia, comparable to those of T cells in normoxia. An increase in IFNγ was observed, and hypoxia reversion by $O_2$-cryogels significantly enhanced secretion of perforin and the serine protease granzyme B. Surprisingly, 50% killing efficiency was restored after only 4 hr, and as low as 0.1% $CaO_2$ was enough to induce a significant increase of perforin and granzyme B secretion after 24 hr. The restoration of this strong cellular immune response using $O_2$-cryogels is likely a result of the reversion of cell hypoxia. Indeed, by preventing the elevation of HIF1α expression, $O_2$-cryogels limited cancer cells aggressiveness mediated by hypoxia-driven signaling. This prevented VEGFα and Wnt11 overexpression as well as hampered the cancer stemness markers CD44 and CD133 upregulation, reducing cancer cell angiogenesis, proliferation, migration, and invasion capacities. In addition, $O_2$-cryogels also inhibited the expression of CD73, resulting in a decrease of the immunosuppressive extracellular adenosine production, crucial for tumor immune escape. Furthermore, oxygenation increases the density of peptide-MHC class I molecules and thereby enhances the recognition and destruction of cancer cells by tumor-specific T cells. This may also contribute to the restoration of cytotoxic T cell effector functions by $O_2$-cryogels in hypoxia.

Injected or compressed $O_2$-cryogels conserved their oxygen-generating capabilities without releasing $CaO_2$ particles that could damage cells or tissues. In contrast, previous oxygen-generating pre-formed hydrogels required surgical implantation and therefore, have limited applications. $O_2$-cryogels can be directly injected at the tumor site for local oxygen delivery and may achieve a higher oxygen tension in some tumors compared to systemic oxygenation, which will restore the ability of cytotoxic T cells to migrate to the tumor site and perform their cytotoxic activities.

In some embodiments, $O_2$-cryogels can have a maximum size of 8×8×1 mm (64 $mm^3$). In other embodiments, $O_2$-cryogels can have a size of 6×6 or 6×8 mm (height× diameter). In some embodiments, injectable $O_2$-cryogels can be as large as 10 mm in diameter. Those implanted using a catheter can be as large as 140 cm in diameter using a French catheter scale of 40. In certain embodiments, the $O_2$-cryogel can have a diameter of 6 mm, 8 mm, 10 mm, or 140 cm. Smaller $O_2$-cryogel size can be attained by breaking larger pieces to make a shapeable injectable paste. In some embodiments, such smaller pieces can have a mean size of 1 μm to 10 cm, such as 10 μm to 10 mm, further such as 50 μm to 2 mm. In other embodiments, such smaller pieces can have a mean size of 1 μm to 10 cm, such as 1 μm to 5 mm, such as 1 μm to 2 mm, further such as 5 μm to 500 μm.

Injectable oxygen-generating cryogels could prove to be a versatile platform for immunotherapy, both as drug delivery vehicles or cancer vaccines. With the clinical approval of immune checkpoint inhibitors for cancer immunotherapy and the recent advances on the implication of hypoxia on immune checkpoint regulation, combining $O_2$-cryogels with CTLA-4 or PD1 blockade is a promising therapeutic strategy. Indeed, anti-tumor T cells de-inhibited by checkpoint blockade are still likely to be suppressed by hypoxia and adenosine which can be prevented by oxygenation. Combination therapy using $O_2$-cryogels and A2A adenosine receptor antagonists might also synergize to improve immunotherapies of cancer by restoring tumor-reactive T-cell functions. Injectable cryogel vaccines have already proven their efficacy for both prophylactic and therapeutic cancer vaccinations against melanoma.

Although they are able to elicit a strong and long-lasting adaptive immune responses to fight cancer, their efficacy in a therapeutic setting is still limited and requires further enhancement. Therefore, using injectable oxygen-generating cryogels as support for cancer vaccination could provide cryogel-based vaccines by both initiating an effective anti-tumor immune response while reversing tumor hypoxia-induced immunosuppression.

Disclosed herein are methods of reducing hypoxia in a biological tissue, comprising administering to the biological tissue an oxygen-generating cryogel (e.g., a macroporous nanocomposite oxygen-generating cryogel); wherein the administration is by injection, catheter, or surgery. In some embodiments, the cryogel comprises a peroxide, an oxide or a percarbonate. In certain embodiments, the cryogel comprises $CaO_2$, $(Na_2CO_3)_2 \cdot 1.5H_2O_2$, $MgO_2$, encapsulated $H_2O_2$/Polyvinylpyrrolidone, magnesium peroxide, hydrogen peroxide, manganese dioxide, zinc oxide, or sodium percarbonate. In some embodiments, the cryogel comprises catalase and $CaO_2$, where the catalase can be acrylate-PEG-Catalase. A lyoprotectant can be used to prevent damage of catalase during cryopolymerization and lyophilization. Such lyoprotectants include, but are not limited to, sucrose, trehaloze, and mannitol.

In certain embodiments, the cryogel comprises one or more checkpoint inhibitors selected from one or more adenosine receptor antagonists for A2a, A2b or A3 receptors, anti-CTLA4, anti-PD1, and anti-PD-L1. In some embodiments, the one or more adenosine receptor antagonists include, but are not limited to, ZM241385; 1,7-methylxantine; theophylline; theobromine; SCH 58261 [7-(2-phenylethyl)-5-amino-2-(2-furyl)-pyrazolo-[4,3-e]-1,2,4-triazolo [1,5-c]pyrimidine]; and KW-6002 [(E)-1,3-diethyl-8-(3,4-dimethoxystyryl)-7-methyl-3,7-dihydro-1H-purine-2,6-dione].

In some embodiments, hypoxia is reduced such that oxygen tissue tension is higher than 5% oxygen. In other embodiments, the cryogel releases oxygen for at least about 4 hr, at least about 16 hr, at least about 24 hr, or at least about 48 hr, or at least about 96 hr. In some embodiments, the cryogel increases oxygen concentration in the biological tissue to physioxic (5% to 14% oxygen) or normoxic (21% oxygen) levels. In some embodiments, hypoxia-induced immunosuppression of one or more of T cells, B cells, and myeloid cells is reduced or reversed compared to immunosuppression levels in hypoxic biological tissue. In other embodiments, wherein extracellular adenosine concentration in hypoxic biological tissue decreases to levels present in normoxic biological tissue.

In some embodiments, the biological tissue is a tumor. In certain embodiments, the tumor is a solid tumor selected from melanoma, renal cell carcinoma, prostate cancer, breast cancer, lung cancer, pancreatic cancer, glioblastoma, ovarian cancer, colon cancer, sarcoma, nasopharyngeal cancer, head and neck cancer, and lymphoma.

In some embodiments, administration of the cryogel is performed by injection, such as with a hypodermic needle. In other embodiments, administration of the cryogel is performed using a catheter or surgery.

Disclosed herein are methods of treating cancer, comprising administering into a tumor of a mammal an effective amount of an oxygen-generating cryogel (e.g., a macroporous nanocomposite oxygen-generating cryogel); wherein the administration is by injection, catheter or surgery; and the cryogel comprises polymerized hyaluronic acid glycidyl methacrylate, acrylate-PEG-G4RDGSP, acrylate-PEG-Catalase, and $CaO_2$. In some embodiments, the cryogel comprises a lyoprotectant selected from sucrose, trehaloze, and mannitol. In other embodiments, the cryogel comprises one or more checkpoint inhibitors selected from one or more adenosine receptor antagonists for A2a, A2b or A3 receptors, anti-CTLA4, anti-CD73 anti-PD1, and anti-PD-L1. Exemplary adenosine receptor antagonists include, but are not limited to, ZM241385; 1,7-methylxantine; theophylline; theobromine; SCH 58261 [7-(2-phenylethyl)-5-amino-2-(2-furyl)-pyrazolo-[4,3-e]-1,2,4-triazolo[1,5-c]pyrimidine]; and KW-6002 [(E)-1,3-diethyl-8-(3,4-dimethoxystyryl)-7-methyl-3,7-dihydro-1H-purine-2,6-dione]. In some embodiments, the cryogel comprises further immunological checkpoint blockade inhibitors.

In some embodiments, the cryogel releases oxygen for at least about 4 hr, at least about 16 hr, at least about 24 hr, or at least about 48 hr, or at least about 96 hr. In certain embodiments, the cryogel increases oxygen concentration in the biological tissue to physioxic or normoxic levels.

In some embodiments, the tumor is a solid tumor selected from melanoma, renal cell carcinoma, prostate cancer, breast cancer, lung cancer, pancreatic cancer, glioblastoma, ovarian cancer, colon cancer, sarcoma, nasopharyngeal cancer, head and neck cancer, and lymphoma. In some embodiments, administration of the cryogel is performed by injection, such as with a hypodermic needle. In other embodiments, administration of the cryogel is performed using a catheter or surgery.

EXEMPLIFICATION

The invention now being generally described, it will be more readily understood by reference to the following examples, which are included merely for purposes of illustration of certain aspects and embodiments of the invention and are not intended to limit the invention.

Materials and Methods

Chemical Modification

Conjugation of hyaluronic acid (HA) with glycidyl methacrylate (GM) was performed as previously described. Briefly, 5 g of HA salt (Sigma-Aldrich, St. Louis, MO, USA)

was dissolved in 1 L phosphate buffered saline (PBS, Sigma-Aldrich, pH 7.4) prior to mixing with 335 mL of dimethylformamide (DMF, Sigma-Aldrich), 62 mL of GM (Sigma-Aldrich), and 46 ml of Triethylamine (TEA, Sigma-Aldrich). The mixture was precipitated in a large excess of acetone after 10 days reaction, filtered using Whatman paper grade 4, and then subsequently dried in a vacuum oven overnight at RT. The resulting product, HAGM, was characterized by $^1$H NMR.

Rhodamine-labeled HAGM (R-HAGM) was prepared by reacting NHS-Rhodamine to amine terminated HAGM ($NH_2$-HAGM) as previously described. Briefly, $NH_2$-HAGM was synthesized by dissolving 1 g of HAGM in 100 mL of 0.1M MES (2-(N-Morpholino) ethane sulfonic acid) solution at pH 5.5. Next, 4 g of adipic acid dihydrazide (AAD, Sigma-Aldrich) and 90 mg of 1-Ethyl-3-(3-dimethylaminopropyl)-carbodiimide (EDC, Sigma-Aldrich) were added to the reaction mixture. The solution was stirred at room temperature (RT) for 4 hr to allow the amination reaction of HAGM to proceed. $NH_2$-HAGM was then precipitated in a large excess of acetone, filtered, and then dried in a vacuum oven overnight at RT. Next, 1 g of $NH_2$-HAGM was dissolved in 10 mL of $NaHCO_3$ (sodium bicarbonate) buffer solution at pH 8.5, and then mixed with 10 mg of NHS-Rhodamine (5/6-carboxy-tetramethyl-rhodamine succinimidyl ester, Fisher Scientific, Waltham, MA, USA). After 16 hr reaction, R-HAGM was precipitated in a large excess of acetone, filtered, and finally dried at RT as described above.

Acrylate-PEG-G4RGDSP (APR) was synthetized by coupling amine-terminated G4RGDSP (GGGGRDGSP) peptide (Peptide 2.0, Chantilly, VA, USA) to an acrylate-PEG-N-hydroxysuccinimide (JenKem Technology, Plano, TX, USA) (molar ratio 1:1). Briefly, 100 mg of acrylate-PEG-Nhydroxysuccinimide and 22.3 mg of G4RGDSP peptide were mixed in $NaHCO_3$buffer solution at pH 8.5, allowed to react for 4 hr at RT, and then finally freeze-dried overnight. Similarly, acrylate-PEG-Catalase (APC) was synthetized by coupling catalase enzyme (Sigma-Aldrich) to acrylate-PEG-N-hydroxysuccinimide co-monomers (JenKem Technology) (molar ratio 1:3).

$O_2$-Cryogels Preparation $O_2$-cryogels (square-shaped, 4×4×1 mm) were fabricated by redox-induced free-radical cryopolymerization in d-$H_2O$ at −20° C. Briefly, 40 mg of HAGM (4%, wt/vol) were mixed with 8 mg of APR (0.8%, wt/vol) and 10 mg of APC (1%, wt/vol) in 1 mL d-$H_2O$ with various amounts (0-1% wt/vol) of calcium peroxide particles ($CaO_2$, Sigma-Aldrich). Then, tetramethylethylenediamine (TEMED, Sigma-Aldrich) (0.28% wt/vol) and ammonium persulfate (APS, Sigma-Aldrich) (0.56% wt/vol) were added to the previous precooled polymer solution at 4° C. The solution was poured into Teflon® molds, transferred to a freezer preset at −20° C., and cryopolymerized for 16 hr. Finally, $O_2$-cryogels were brought to RT to remove ice crystals, and then washed with d-$H_2O$. For microscopy imaging, 0.3% wt/vol of HAGM in each formulation was substituted with R-HAGM to label the polymer walls.

$CaO_2$ Encapsulation within $O_2$-Cryogels

Encapsulation efficiency of $CaO_2$ within the polymer walls of $O_2$-cryogels was determined by Alizarin Red S staining. A 2% wt/vol Alizarin Red S (Sigma Aldrich) solution was freshly prepared in d-$H_2O$ and adjusted to pH 4.2. $O_2$-cryogels were incubated with Alizarin S for 20 min, rinsed with d-$H_2O$ several times until the washing solution was clear, and photographed via a Canon camera or via confocal microscopy using a Leica TCS SP5 X WLL Confocal Microscope (Buffalo Grove, IL, USA). $CaO_2$ distribution in the polymer walls as well as the microstructural features of $O_2$-cryogels were characterized by scanning electron microscopy (SEM) and Energy Dispersive X-Ray Analysis (EDX). First, $O_2$-cryogels were freeze-dried for 24 hr, mounted on sample holder using carbon tape, and then sputter-coated with up to 5 nm of thickness of platinum/palladium. Next, samples were then imaged using secondary electron detection on a Hitachi S-4800 SEM at 25 kV voltage and 10 µA current. Pore sizes were determined using Fiji, Analyze Particles, and Diameter J plugins softwares.

$O_2$-Cryogels Physical Characterization

The swelling ratio was determined using a conventional gravimetric procedure, as previously described. Briefly, cylindrical $O_2$-cryogels (6-mm diameter, 6-mm height) were prepared and immerged in PBS for 24 hr at 37° C. prior measurement. Then, the equilibrium mass swelling ratio ($Q_m$) was calculated by dividing the mass of fully swollen $O_2$-cryogel (ms) by the mass of freeze dried $O_2$-cryogel (md). $O_2$-cryogels were washed in d-$H_2O$ prior to freeze-drying.

$$Qm = \frac{m_s}{m_d}$$

The degree of pore connectivity was evaluated by using a water-wicking technique. Fully hydrated disc-shaped $O_2$-cryogels (6-mm diameter, 1-mm height) were first weighed on an analytical scale. Next, a Kimwipe was used to wick away free water within interconnected pores, and gels weighed a second time. The degree of pore connectivity was then calculated as the volume of water (%) wicked away from the gels.

Young's moduli were determined using an Instron 5944 (Instron, Norwood, MA, USA). Cylindrical cryogels (6-mm diameter, 8-mm height) were dynamically deformed (at a constant rate) between two parallel plates for 10 cycles (strain rate of 10% per minute) while being constantly hydrated in PBS (pH 7.4). Compressive strain (mm) and load (N) were then quantified at the 8th cycle using an Instron's Bluehill 3 software. Young's Moduli were determined by measuring the tangent of the slope of the linear region on the loading stress/strain curve.

Enzymatic Activity of Catalase ($H_2O_2$ Depletion).

Catalase and APC enzymatic activity were assessed using a fluorimetric hydrogen peroxide assay Kit (Sigma-Aldrich). Briefly, enzymes were prepared at different concentrations (0.1-5 u/mL), mixed with 30 µM of $H_2O_2$, and incubated at 37° C. for 30 min. Then, the fluorescence intensity (Ex/Em=540/590 nm) was recorded using a synergy HT plate reader (Biotek, Winooski, Vermont, USA) to quantify residual $H_2O_2$ concentration in the solution. To evaluate potential $H_2O_2$ depletion from $O_2$-cryogels, cryogel samples were incubated in d-$H_2O$ at 37° C. for 15 min then transferred into 96 well plates and assessed using the fluorimetric hydrogen peroxide assay kit, as described above.

Oxygen Release Kinetics of $O_2$-Cryogels

Oxygen release kinetics of $O_2$-cryogels were determined by using needle-type optical oxygen microprobes (PyroScience GmbH, Aachen, Germany) under normoxic and hypoxic conditions. Briefly, cylindrical $O_2$-cryogels (6-mm diameter, 8-mm height) were individually placed into 2 mL Eppendorf tubes containing 1.8 mL of Dulbecco's Modified Eagles Medium (DMEM) (Corning, Corning, NY, USA) and incubated at 37° C. in normoxic (20% oxygen) or hypoxic (1% oxygen) conditions. The needle-type probe was positioned in the center of cryogels prior to recording the dissolved oxygen concentration (mol/L, 1 point every 300 seconds). Oxygen release was then monitored up to 4 days Additionally, to mimic syringe injection conditions, $O_2$-cryogels were compressed up to 90% of their volume prior to performing additional oxygen measurements. Briefly, cylindrical cryogels were allowed to swell in PBS until equilibrium prior to being mechanically compressed between two parallel plates. Next, compressed cryogels were re-swollen back to their initial shape and size in DMEM and oxygen release was monitored up to 4 days at 37° C. under normoxic conditions.

Cell Culture and Seeding of $O_2$-Cryogels

Melanoma cells (B16-F10, CRL-6475, ATCC, Rockville, MD, USA) were cultured in complete DMEM: DMEM supplemented with 10% Fetal Bovine Serum (FBS, Sigma-Aldrich), 100 g/mL penicillin (Fisher Scientific) and 100 g/mL streptomycin (Fisher Scientific). B16-F10 ovalbumin (OVA) expressing cells (B16-ova, kindly provided by Prof. M. Sitkovsky) were cultured in complete DMEM supplemented with 50 g/mL gentamycin (Fisher Scientific). Cells were incubated at 37° C. in either humidified 5% $CO_2$/95% air (normoxia) or humidified 5% $CO_2$/1% $O_2$/94% N2 (hypoxia).

Prior to cell seeding, $O_2$-cryogels were sanitized with 70% ethanol for 15 min then washed several times with sterile water. Next, $O_2$-cryogels were mechanically compressed on sterile gauze to partially remove pore water under sterile conditions. Finally, fifteen microliters of a cell suspension (B16-F10 or B16-ova, $10_7$ cells/mL) in complete DMEM were added drop-wise on top of each square-shaped cryogel and incubated for 1 hr to allow cell adhesion. Cell-laden $O_2$-cryogels were then supplemented with additional complete DMEM for the extent of the experiment. If the experiment required a hypoxic environment, complete DMEM was pre-incubated (conditioned) for at least 1 hr in hypoxia.

Cell Viability Assay

A live/dead assay was performed to evaluate cell viability within $O_2$-cryogels. After 1-day incubation, cell-laden $O_2$-cryogels were incubated for 15 minutes with ViaQuant™ fixable far-red dead cell staining according to manufacturer's instructions (Genecopoeia, Rockville, MD, USA). Next, cell-laden $O_2$-cryogels were rinsed with PBS, fixed with 4% paraformaldehyde (PFA, Sigma Aldrich) for 20 minutes at RT, and then washed with PBS. Prior to microscopy imaging, cells were permeabilized with PBS supplemented with 0.1% triton X-100 (Sigma Aldrich) for 5 min, stained with Alexa Fluor 488-phalloidin (Cell Signaling Technology, Danvers, MA, USA), and then with DAPI (Sigma Aldrich) according to manufacturer's protocols. Cells were imaged by confocal microscopy using a Leica TCS SP5 X WLL Confocal Microscope. Tile pictures were recreated from 5 individual $O_2$-cryogel samples to image the entire gel dimension, and cell viability was calculated by Fiji software as the ratio between dead (far-red fluorescence surface area) and the total cell number (blue or green fluorescence surface area). For each condition, one representative high-resolution stacked image was collected with 2 μm separation between slices (z-stacks).

Minimally Invasive Delivery and Biocompatibility Assays

Seven-week old female C57BL/6J mice (n=4; The Jackson Laboratory, Bar Harbor, Maine, USA) were anesthetized with isoflurane (4-5% for induction, 1-3% for maintenance) in oxygen using an inhalation anesthesia system (300 SERIES vaporizers, VSS, Rockmart, GA, USA). $O_2$-free cryogels and $O_2$-cryogels were suspended in 0.2 mL of PBS and subcutaneously injected in both dorsal flanks of each mouse using a 16-gauge needle. After 7 days, mice were euthanized and cryogels explanted with the surrounding tissues. Next, each sample was fixed for 48 hr in 4% PFA, embedded in paraffin, cryosectioned into 5-μm-thick slices, and then stained for histological analysis with hematoxylin and eosin (H&E) and Masson's Trichrome (MT). Animal work was conducted in compliance with the National Institutes of Health (NIH) guidelines and approved by the division of laboratory animal medicine (DLAM) and Northeastern University institutional animal care and use committee (IACUC) (protocol number 17-0828R).

Hypoxia Detection Assays

Cellular hypoxia within $O_2$-cryogels was determined by using hypoxyprobe kit according to manufacturer's recommendation (Hypoxyprobe, Burlington, Massachusetts, USA). Briefly, after 24 hr incubation in normoxia or hypoxia, cell-laden $O_2$-cryogels were incubated for 2 hr with 200 μM Hypoxyprobe™-1 in complete DMEM. Next, cell-laden scaffolds were fixed, permeabilized, and immunostained with mouse MAb1 antibody and rabbit anti-mouse IgG (H+L) Alexa Fluor 488 secondary antibody (Fisher Scientific). Cryogel samples were then imaged by confocal microscopy using a Leica TCS SP5 X WLL Confocal Microscope. Fractions of cellular hypoxia was calculated using Fiji software, based on the ratio between hypoxic (green fluorescence surface area) and the total number (blue surface area) of cells.

Adenosine concentration was quantified using fluorometric adenosine assay kit (Biovision, San Francisco, California, USA) following manufacturer's protocol. After 24 hr incubation, either in normoxia or hypoxia, supernatants from each cell-laden $O_2$-cryogel sample were collected, mixed with the reactant, and then the fluorescence intensity (Ex/Em=535/587) was recorded using a synergy HT plate reader (Biotek) for measuring adenosine concentration.

Gene expression of HIF1α, Wnt11, VEGFa, CD73, and HPRT was assessed with RT-qPCR. After 24 hr incubation, either in normoxia or hypoxia, the total RNA from cell-laden $O_2$-cryogel samples was extracted using PureLink™ RNA Mini Kit (Fisher scientific) according to the manufacturer protocol.

Next, a 2-step RT-qPCR was conducted. First, the reverse transcription of RNA to cDNA was conducted using a High Capacity cDNA Reverse Transcription Kit (Fischer scientific) on a MyCycler (Biorad, Hampton, NH, USA). Then, the following genes were measured using TaqMan® Gene Expression Assays (Fisher scientific) on an Mx3005P QPCR system (Agilent, Santa Clara, CA, USA): HIF1α: Mm00468869_m1, Wingless-type MMTV integration site family member 11 (Wnt11): Mm00437327_g1, Vascular growth factor α (VEGFα): Mm00437306_m1, CD73: Mm00501915_m1, CD44: Mm01277163_m1, CD133: Mm00477115_m1, and HPRT (housekeeping gene): Mm03024075_m1.

Cytotoxicity Assay in a B16-OVA Melanoma Model

Prior to cell seeding in $O_2$-cryogels, B16-ova cells were stained with 10 μM CFSE (Biolegend, San Diego, CA, USA) for 15 min at 37° C. according to manufacturer's protocol. Next, $1.5 \times 10^5$ cells in complete RPMI (Roswell Park Memorial Institute medium supplemented with 10% FBS, 100 g/mL penicillin, and 100 g/mL streptomycin) were seeded onto square-shaped $O_2$-cryogels and subsequently incubated in normoxia. After 3 hr of incubation, splenocytes in complete RPMI ($2 \times 10_5$—ratio target-effector 1:2) isolated from OT-1 RAG mice (The Jackson Laboratory, Bar Harbor, ME, USA) were added into each well. Splenocytes were pre-stimulated with anti-CD3 (Clone 145-2C11, Fisher Scientific) and anti-CD28 (Clone 37.51, Fisher Scientific) monoclonal antibodies for 48 hr according to manufacturer's recommendation. If the experiment required a hypoxic environment, complete RMPI, splenocytes suspension, and B16-ova-laden $O_2$-cryogels were pre-incubated (conditioned) for 1 hr in hypoxia prior to co-culture. Following a 24 hr-incubation period of B16-ova/splenocytes co-culture: (i) the supernatants were collected to quantify IFNγ, TNFα, granzyme B (DuoSet Elisa, R&D system, Minneapolis, MN, USA) and perforin (GBiosciences, Saint Louis, MO, USA) secretion by ELISA; and (ii) the cytotoxic activity of OT-1 cells was examined using a cell viability assay as described previously.

Additionally, the cytolytic activity of OT-1 T cells towards B16-ova cells was monitored using time-lapse microscopy. First, under normoxic conditions, $1\times10^5$ B16-ova cells in complete RPMI were seeded in a 24-well plate for 3 hr to allow cell adhesion. Next, $2\times10^5$ activated splenocytes in complete RPMI (ratio target-effector 1:2) with either $CaO_2$-free square-shape cryogels or 0.5% $O_2$-cryogels were added to each well (total volume=500 L). Complete RPMI media, splenocytes suspension, and the 24-well plate seeded with B16-ova cells were pre-incubated (conditioned) for 1 hr in hypoxia prior to co-culture. Next, time-lapse experiments were performed using a bright field inverted microscope (Zeiss Axio Observer Z1, Zeiss, Oberkochen, Germany) at 37° C. in hypoxic conditions (5% $CO_2+1\%$ $O_{2+94}\%$ $N_2$) using a closed chamber. One preselected region of each well (350×350 μm) was captured and recorded every 10 min for 4 hr.

In Vitro Dendritic Cell (DC) Activation Assay

BMDCs were extracted from C57BL/6 femur bone marrow (The Jackson Laboratory) as described by Madaan et al., then cultured for 6 days in RPMI 1640 supplemented with 10% heat-inactivated FBS, 100 μg/mL penicillin, 100 μg/mL streptomycin and 20 ng/mL recombinant mouse GM-CSF (Genscript). To evaluate DC activation, DCs were seeded in p24 well plates at a density of $2.5\times10^6$ cells/mL, in presence or absence of 0% and 0.5% $O_2$-cryogels, and then stimulated with soluble LPS (100 ng/mL) or soluble CpG ODN 1826 (5 μg/mL) for 24 hr. If the experiment required a hypoxic environment, complete media, DC suspension, and $O_2$-cryogels were conditioned for 1 hr in hypoxia prior seeding and stimulation with LPS or CpG ODN. BMDC maturation was then analyzed by flow cytometry (BD FACSCalibur DxP upgraded, Cytek Bioscience) using the following anti-mouse fluorescent antibodies (Biolegend): MHC II (M5/114.15.2, Rat IgG2b, PE/Cy7), CD86 (GL 1, rat IgG2a, PE), CD317 (927, Rat IgG2b, BV421) and CD11c (N418, hamster IgG, APC). Cytokine levels (IL-12p70, IL-6, and TNF-α) in the cell culture supernatant were analyzed by ELISA (ELISA MAX Deluxe, Biolegend) according to the manufacturer's instructions.

Statistical Analysis

All data are presented as mean±SEM. Statistical analyses were performed using GraphPad Prism Software (La Jolla). Significant differences between groups were analyzed by a one-way analysis of variance (ANOVA) and Dunnett or Bonferroni post-test. Differences were considered statistically significant for p values less than 0.05.

Example 1. Fabrication of HAGM-Based Oxygen-Generating Cryogels ($O_2$-Cryogels)

Oxygen-generating cryogels were fabricated using free radical cryopolymerization at −20° C. (4% HAGM, 0.8% APR, 1% APC), using various concentrations of $CaO_2$ (from 0 to 1 wt/vol %. (FIG. 1A). These cryogels were prepared using HAGM to mimic aspects of the TME, "APR" to enhance cell-scaffold interaction and prevent anoikis, APC to deplete rapidly $H_2O_2$ byproduct, and $CaO_2$ to release oxygen from cryogels ($O_2$-cryogels). During the cryopolymerization process (reaction at −20° C.), a phase separation of macromonomers, $CaO_2$, and initiators from ice crystals (frozen water) occurred (step 1), allowing polymerization within this non-frozen liquid phase—allowing entrapment of $CaO_2$ particles into newly formed and tightly crosslinked polymer walls (step 2). Once the reaction is completed (about 17 hr), cryogels were allowed to thaw at RT to melt ice crystals that acted as porogens, generating scaffolds with large and highly interconnected macropores (step 3). Cryogels were subsequently washed with d-$H_2O$ to remove any unreacted precursors. Unlike other macroscale preformed oxygen-generating biomaterials, $O_2$-cryogels can withstand deformation and compression up to 90% of their volume, resulting in biomaterials that can overcome shear-stress and undergo injection through conventional needle (e.g., 16-gauge, 18-gauge, etc) (step 4). Moreover, $O_2$-cryogels can controllably release oxygen in presence of $H_2O$ via $CaO_2$ hydrolysis.

Example 2. Characterization of $O_2$-Cryogels

Figure 2A:
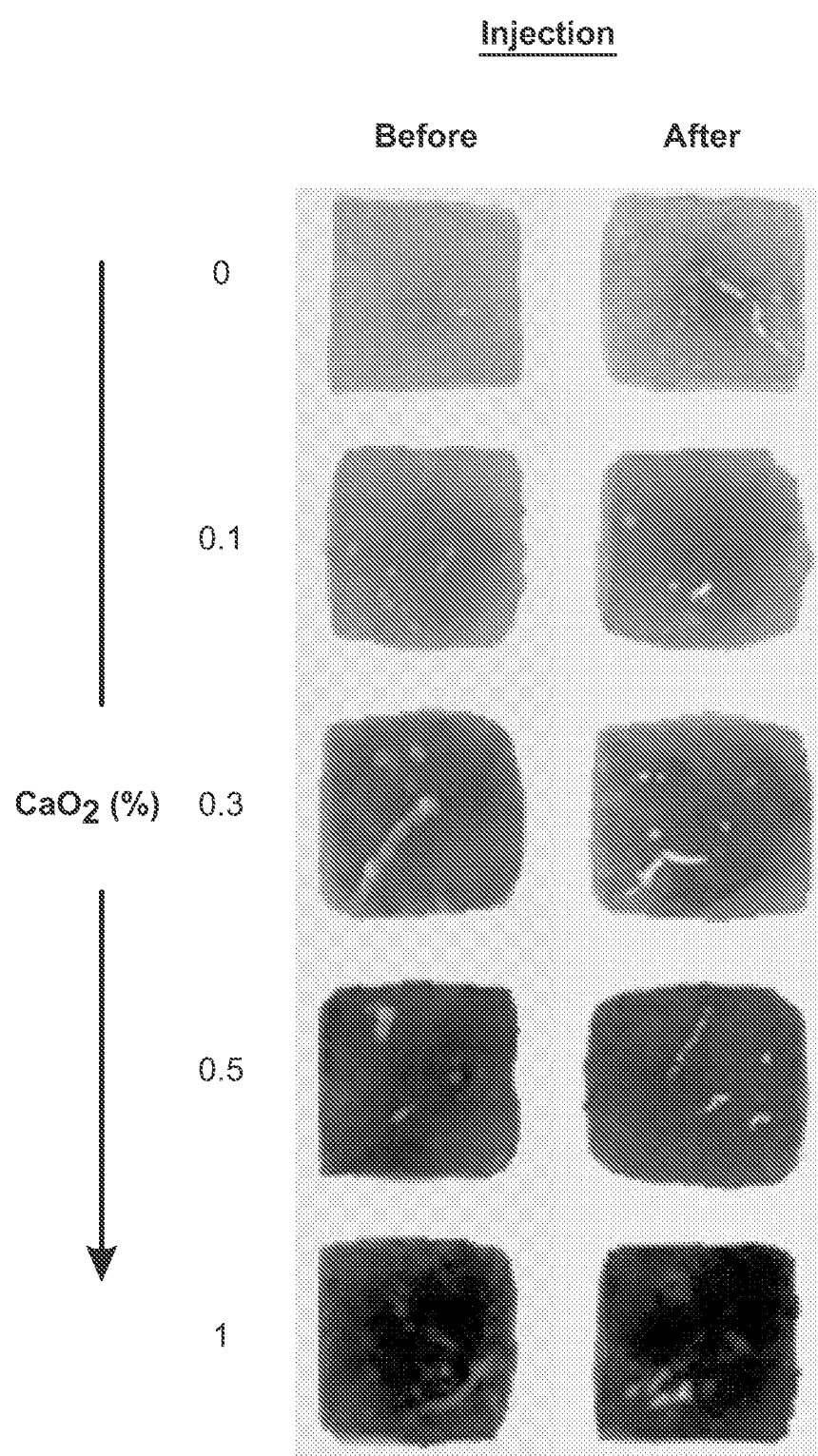
FIG. 2A-FIG. 2P depict physical features of $O_2$-cryogels.
Figure 2J:
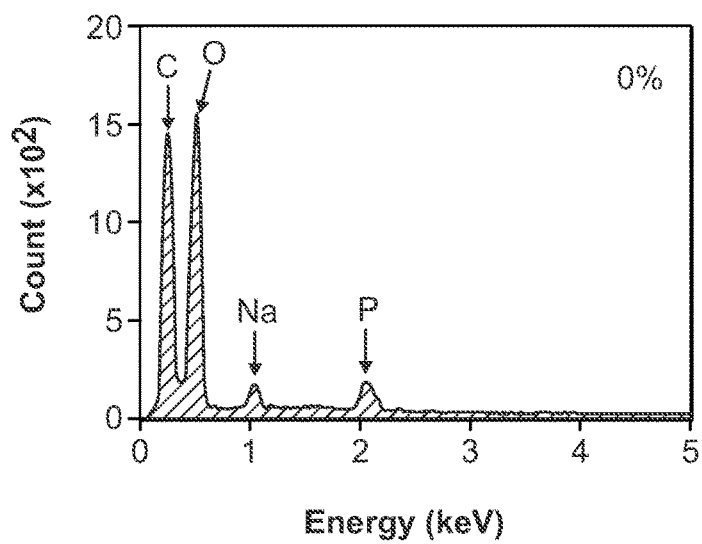
FIG. 2J is an elemental analysis of a non-oxygenated cryogel.
Figure 2K:
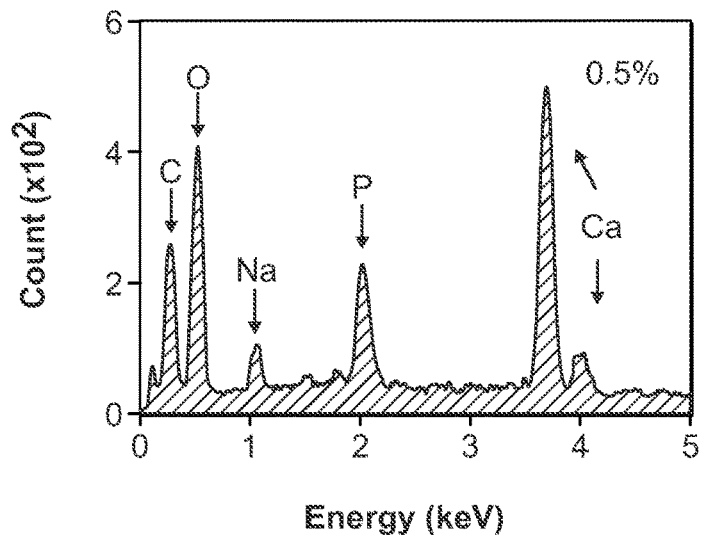
FIG. 2K is an elemental analysis of a 0.5% $O_2$-cryogel.
Figure 8:
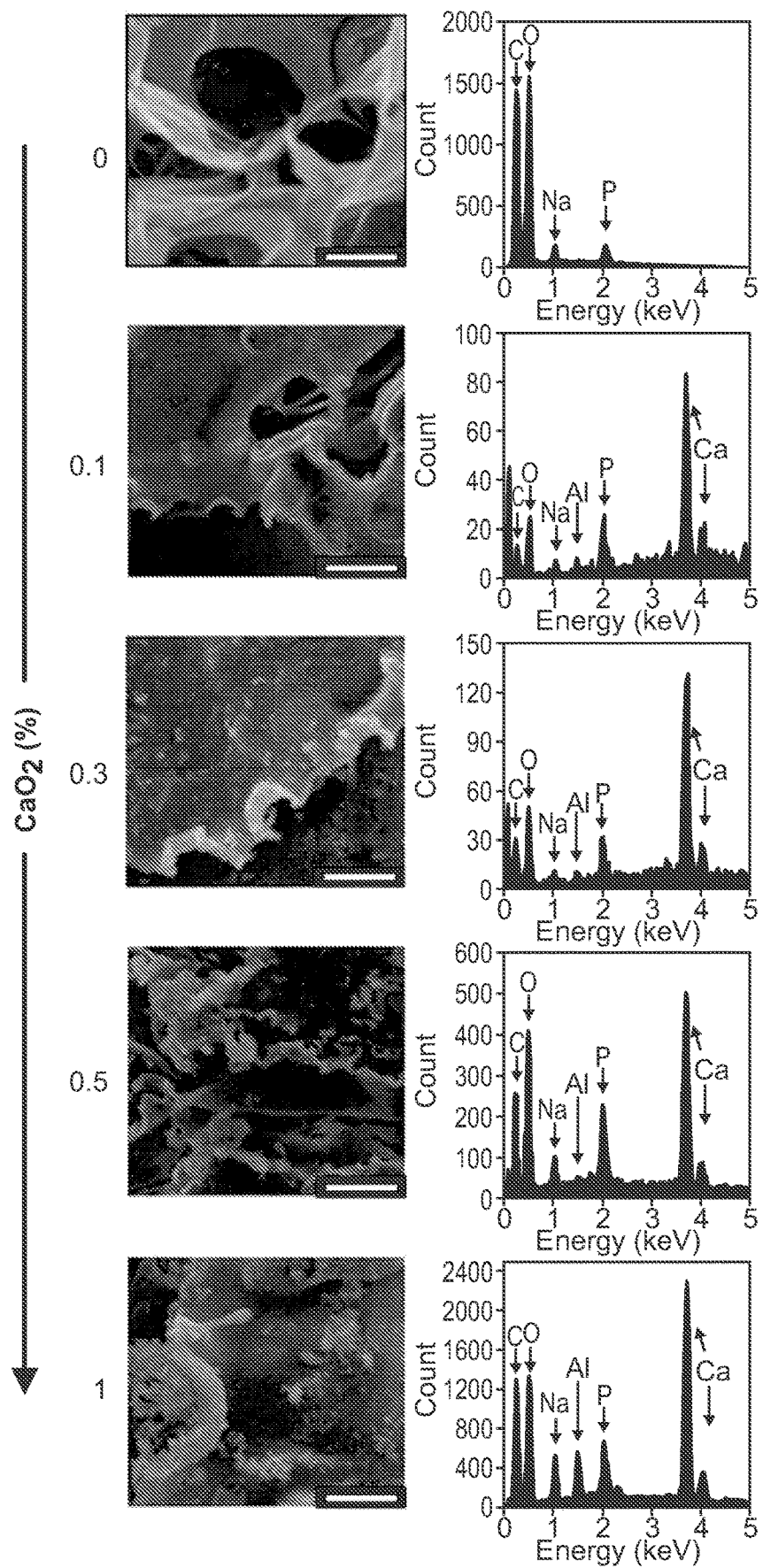
FIG. 8 depicts EDX elemental analysis of cryogels and $O_2$-cryogels prepared with 0.1%, 0.3%, 0.5%, and 1% (wt/v) $CaO_2$ nanoparticles. SEM pictures (left) correspond to the area analyzed by EDX analysis (right). Scale bars: 25 m.

For controlled and sustained release of oxygen from $O_2$-cryogels, efficient encapsulation and distribution of $CaO_2$ nanoparticles throughout the scaffold was achieved. To demonstrate that $CaO_2$ nanoparticles were successfully and homogeneously incorporated into polymer walls, cryogels ($CaO_2$-free) and $O_2$-cryogels containing different amounts of $CaO_2$ (0.1-1 wt/vol %) were stained with Alizarin Red S before and after injection (FIG. 2A). Alizarin Red S reacts with inorganic calcium and can be visualized as red stains. An increase in red stain intensity was observed proportionally to the increase in $CaO_2$ concentration, confirming the efficient incorporation of these particles within $O_2$-cryogels. Furthermore, $O_2$-cryogels maintained similar shape memory properties as compared to $CaO_2$-free cryogels and no significant changes in Alizarin Red S staining were observed following their injection. These results suggest that $CaO_2$ particles remain physically entrapped within the polymer walls even when shear stress is applied. Confocal microscopy (FIG. 2B-FIG. 2G) combined with SEM images (FIG. 2H-2I, FIG. 7) and EDX analysis (FIG. 2J-FIG. 2K, FIG. 8) of $O_2$-cryogels further confirmed results obtained via Alizarin Red S staining. Indeed, $O_2$-cryogels demonstrated an increase in $CaO_2$ particle entrapment within their polymer walls proportional to the initial loading of $CaO_2$ particles. Additionally, a homogeneous distribution of these particles was observed throughout the entire $O_2$-cryogel construct.

Figure 2L:
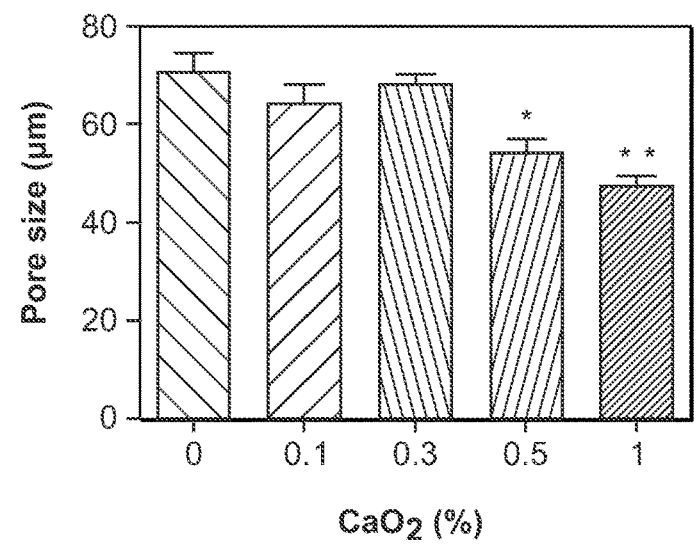
FIG. 2L provides the pore size of cryogels having 0-1% $CaO_2$.
Figure 2N:
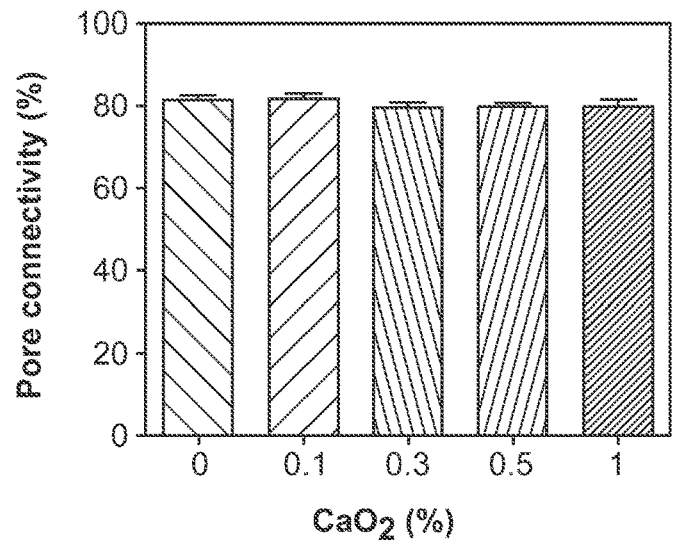
FIG. 2N is a bar graph depicting the pore connectivity of $O_2$-cryogels.
Figure 2O:
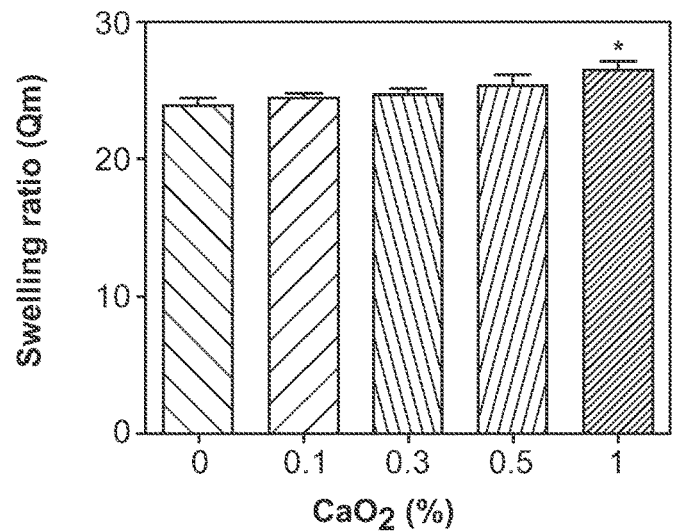
FIG. 2O is a bar graph depicting the mass swelling ratio of $O_2$-cryogels.
Figure 2P:
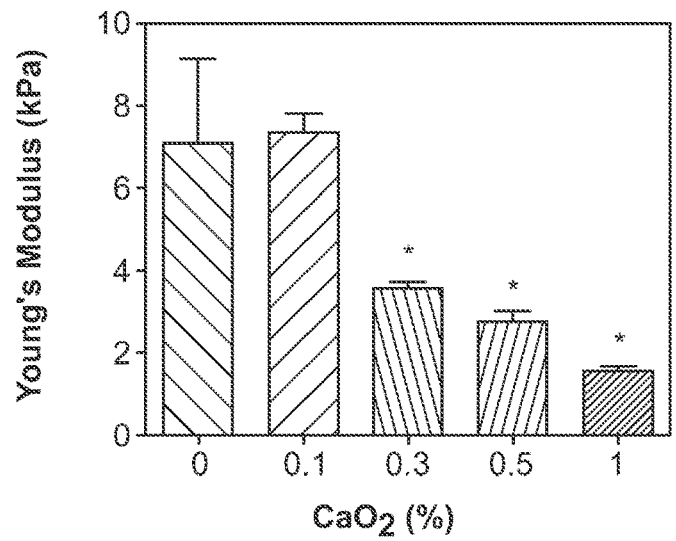

Cryogels typically exhibit a system of highly interconnected macropores and high viscoelasticity. The impact of $CaO_2$ encapsulation on cryogel's physical properties was evaluated by observing macrostructural changes at various $CaO_2$ concentrations (FIG. 2L-FIG. 2M). $O_2$-cryogels displayed large pores ranging from 20 to 100 μm of diameter. However, a decrease of pore size was observed proportionally to the increase in $CaO_2$ concentration from 70.51±10.7 μm ($CaO_2$-free) to 47.43±6.7 μm (1% $CaO_2$)). The mechanical properties of the $O_2$-cryogels were also affected by their network structure as shown in FIG. 2N-FIG. 2P. Although $CaO_2$ did not change the high degree of pore connectivity of $O_2$-cryogels as compared to cryogels (80±3% of pore connectivity) (FIG. 2N), increased $CaO_2$ concentration induced a slight elevation of the swelling ratio from 23.9±0.9 (0% $CaO_2$) to 26.6±0.6 (1% $CaO_2$) (FIG. 2O). Additionally, $CaO_2$ encapsulation significantly impacted the Young's modulus (FIG. 2P). While $CaO_2$-free cryogels displayed a modulus of 7±2 kPa, the increase in $CaO_2$ concentration induced a decrease of the Young's modulus up to 1.5±0.2 kPa for 1% $O_2$-cryogels.

Example 3. Sustained Oxygen Release from $O_2$-Cryogels $CaO_2$ is well known for its capacity to be hydrolyzed in water to release oxygen. The reaction of $CaO_2$ in water is:

$$CaO_2 + 2\ H_2O \rightarrow Ca(OH)_2 + H_2O_2$$

$$2\ H_2O_2 \rightarrow O_2 + 2\ H_2O$$

Figure 3A:
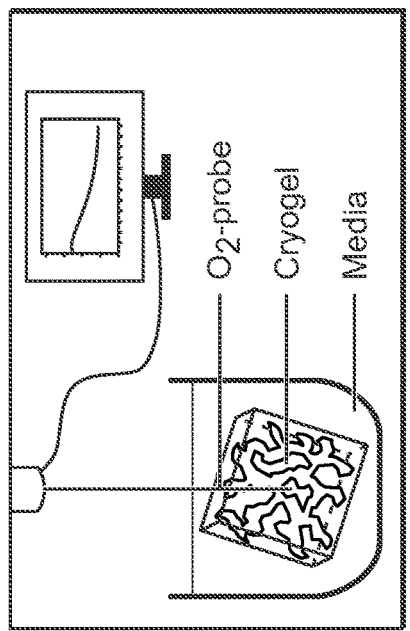
FIG. 3A-FIG. 3E depicts the controlled and sustained release of oxygen from $O_2$-cryogels.
Figure 9A:
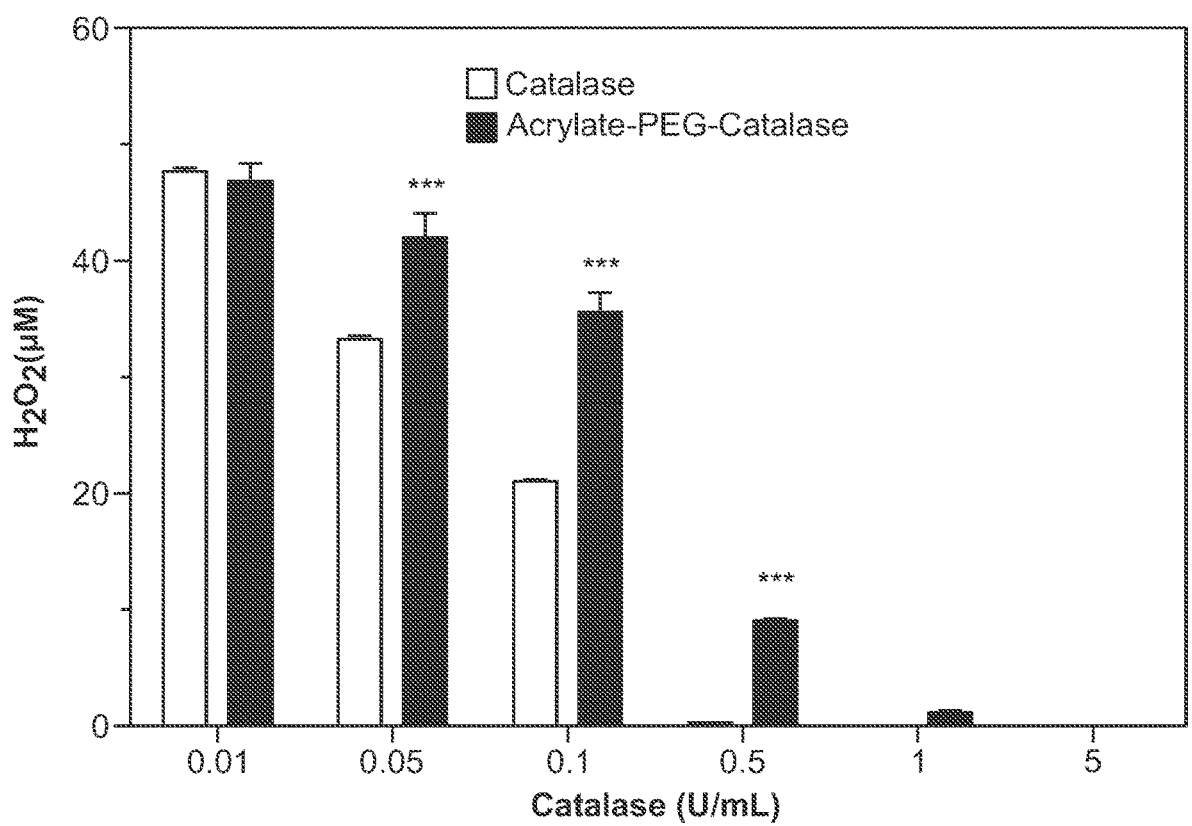

However, this reaction produces $H_2O_2$, a reactive oxygen species (ROS) byproduct, which can induce unwanted side reactions cellular damage leading to cell death, especially at concentrations greater than 10 µM. To overcome this limitation, catalase, an effective enzyme in depleting $H_2O_2$, was first chemically modified, then incorporated in $O_2$-cryogels to sustainably consume $H_2O_2$. As shown in FIG. 9A, the chemical coupling of acrylate-PEG-NHS to catalase (molar ratio 3:1), a step needed for its covalent conjugation during cryogel fabrication, decreased APC activity by 70±3%. Next, the capacity of APC to suppress $H_2O_2$ following cryogelation was investigated. Compared to catalase-free $O_2$-cryogels, catalase-containing $O_2$-cryogels prevented effectively any residual $H_2O_2$ (FIG. 3A) at concentrations: 0.1% to 0.3% $CaO_2$. Low levels of $H_2O_2$, 4±1 µM and 11±2.5 µM, were measured within $O_2$-cryogels containing 0.5% and 1% $CaO_2$, respectively.

Interestingly, APC boosted oxygen production when processing $H_2O_2$ (FIG. 9B). While no oxygen release was observed when catalase-free cryogels were immersed in 50 mM $H_2O_2$, 1% APC-containing cryogels induced the formation of small bubbles, suggesting a quick conversion of $H_2O_2$ into oxygen.

Figure 3B:
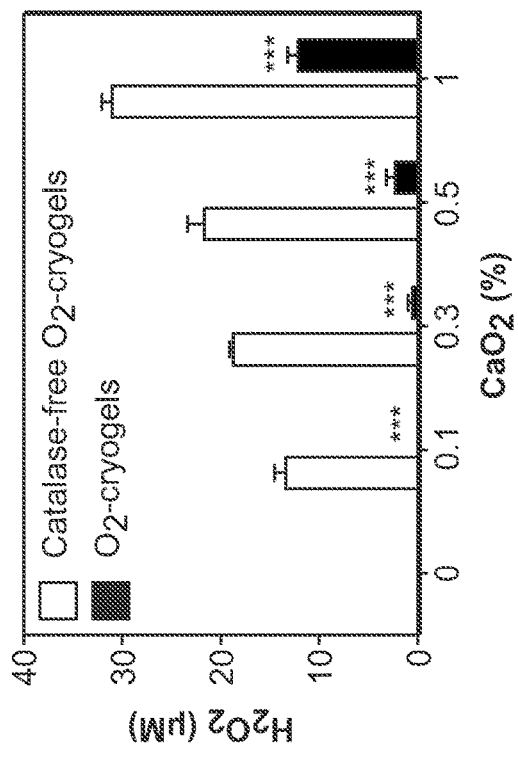
Figure 3C:
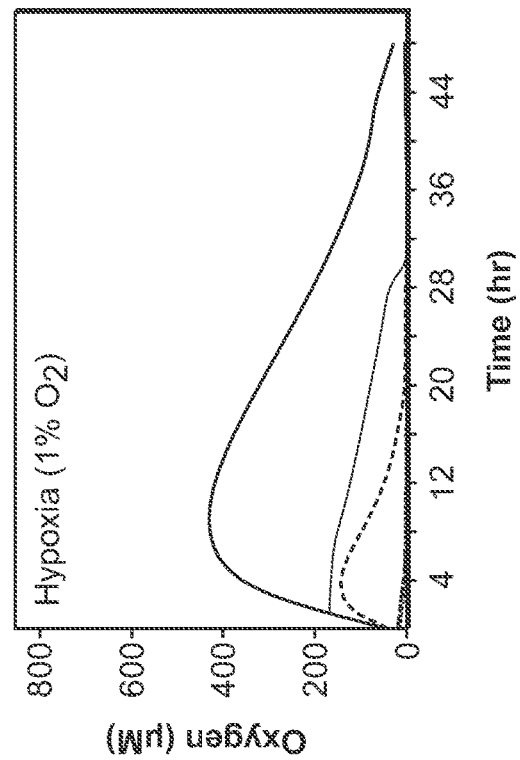
Figure 3D:
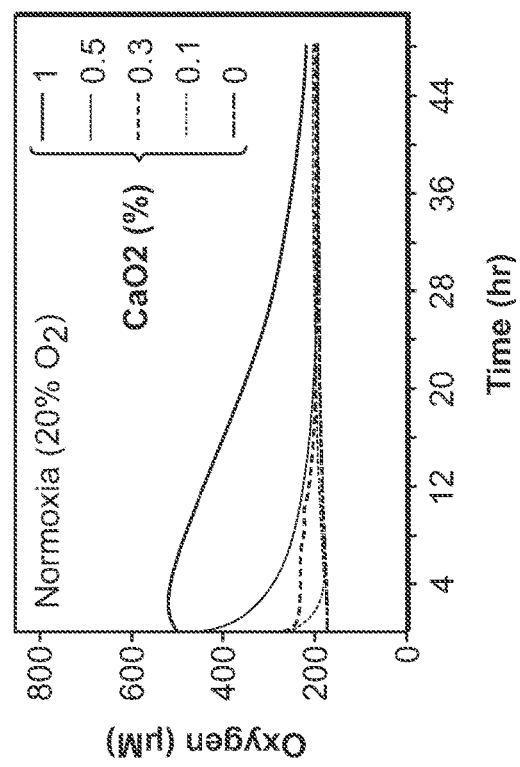
Figure 9C:
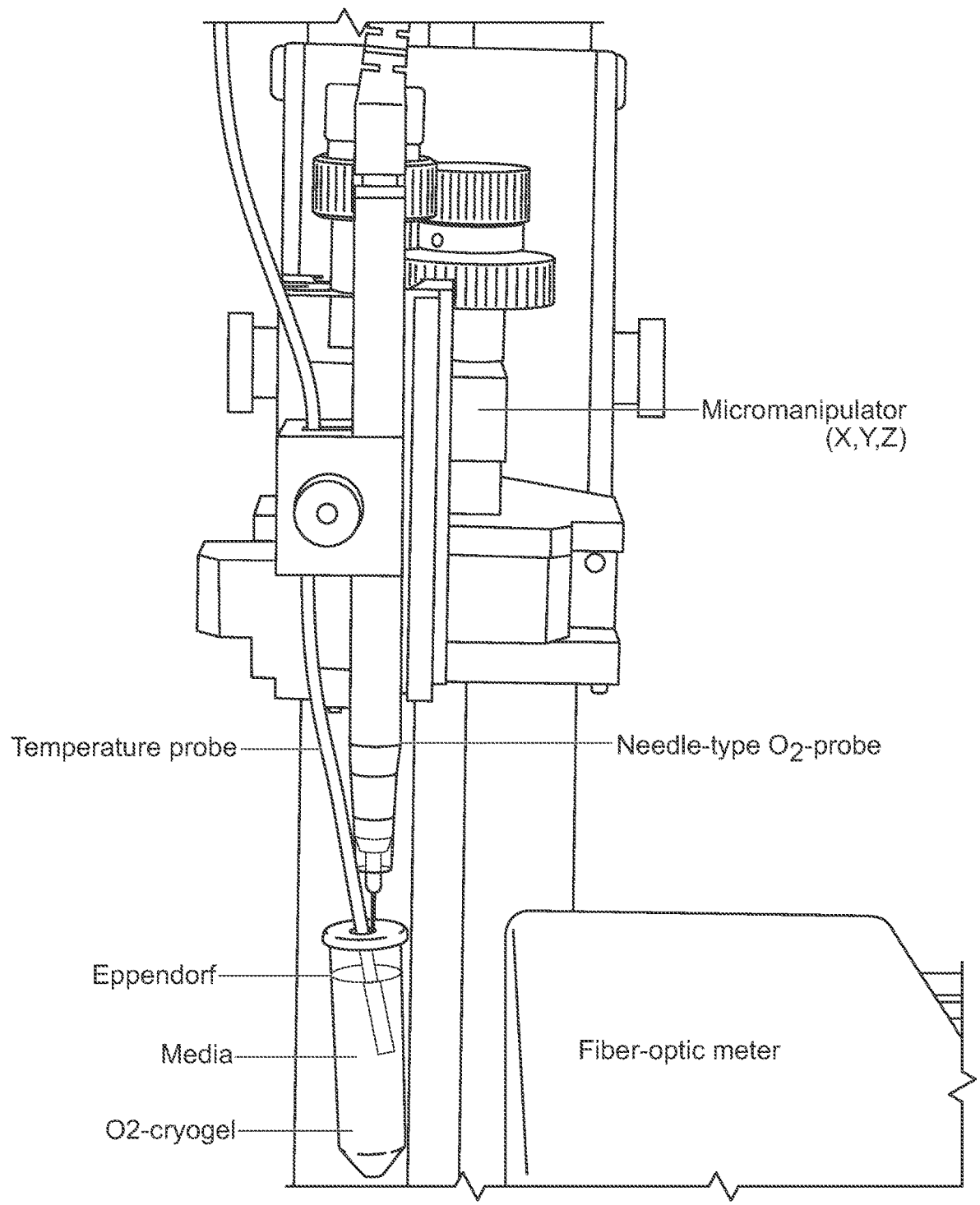

Oxygen release kinetics from cryogels and $O_2$-cryogels containing various amounts of $CaO_2$ (0.1 to 2% wt/vol) were next characterized. Needle-type oxygen probes were positioned in the center of each cryogel and $O_2$-cryogel and the dissolved concentration of oxygen in the media was measured every 5 min for 2 days (FIG. 3B and FIG. 9C). In both normoxic (FIG. 3C) and hypoxic (FIG. 3D) conditions, oxygen-release kinetics were proportional to the amount of $CaO_2$. In normoxia, $O_2$-cryogels induced a maximum oxygen concentration increase by 52%, 65%, 160%, and 215% for $O_2$-cryogels containing 0.1%, 0.3%, 0.5% and 1% $CaO_2$, respectively. This trend was associated with a sustained release of oxygen for 4 hr, 16 hr, 24 hr, 48 hr, and up to 96 hr (FIG. 3C, FIG. 12). As expected, the control cryogels did not release any oxygen. Similar results were observed in hypoxia (FIG. 3D). $O_2$-cryogels increased the maximum oxygen concentration by 160% to 2000% proportional to the initial loading of $CaO_2$ (0.1-1% wt/vol) and allowed a sustained release of oxygen up to 48 hr. Interestingly, $O_2$-cryogels in hypoxic conditions allowed the local reoxygenation and restoration of oxygen levels above physioxia (5-8% oxygen, 80 µM of oxygen at 37° C., 1013 $\hbar$Pa) for 8 hr with 0.3% $CaO_2$, 20 hr with 0.5% $CaO_2$, and 40 hr with 1% $CaO_2$.

Figure 3E:
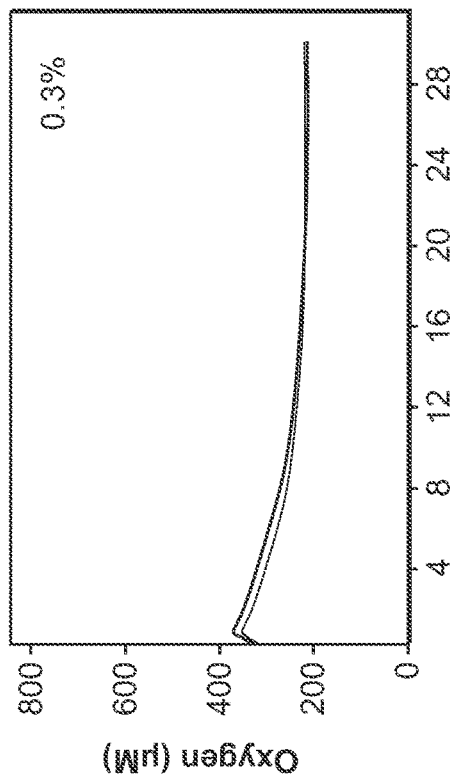
Figure 3F:
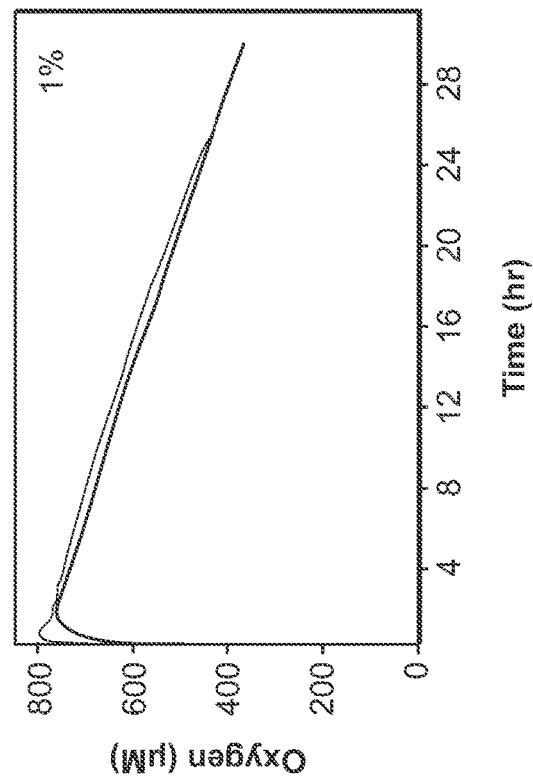
FIG. 3F shows oxygen release after 0.3% compaction.
Figure 3G:
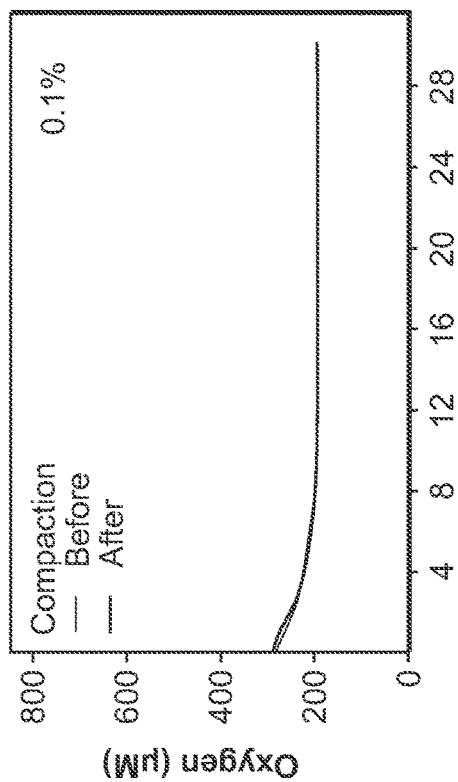
FIG. 3G shows oxygen release after 0.5% compaction.
Figure 3H:
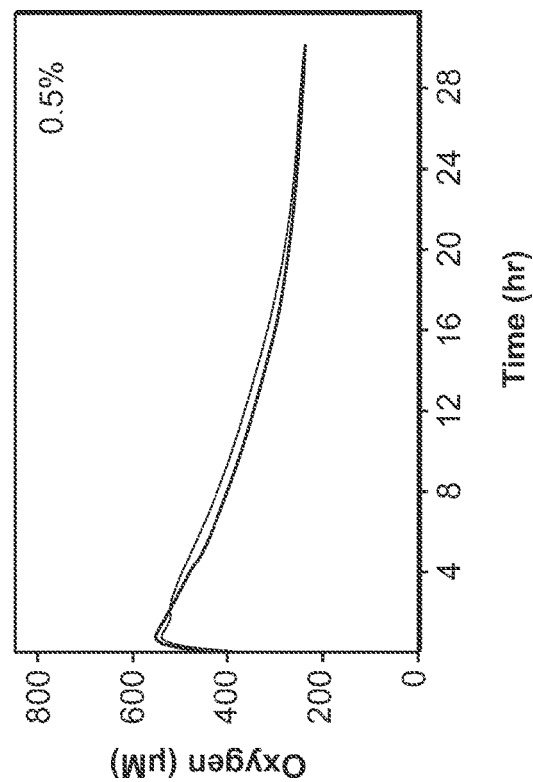
FIG. 3H shows oxygen release after 1% compaction.

These $O_2$-cryogels were designed to be injectable, therefore their capacity to release oxygen efficiently following injection was next evaluated. As large cylindrical-shape cryogels were needed, a compaction up to 90% of their volume in addition to a shear stress was applied to each $O_2$-cryogel to mimic the injection process (FIG. 3E). Independently of the $CaO_2$ concentration, oxygen release kinetics were found to be similar before and after compaction. These results are consistent with $CaO_2$ entrapment measurements and confirm that $O_2$-cryogels can remain intact after syringe injection and retain their capacity to sustain the release of oxygen. Altogether, these results indicate that injectable oxygen-generating cryogels were successfully fabricated and allowed a sustained delivery of oxygen for up to 96 hr in hypoxic and normoxic conditions.

Example 4. Cytocompatibility and Biocompatibility of $O_2$-Cryogels

Figure 4B:
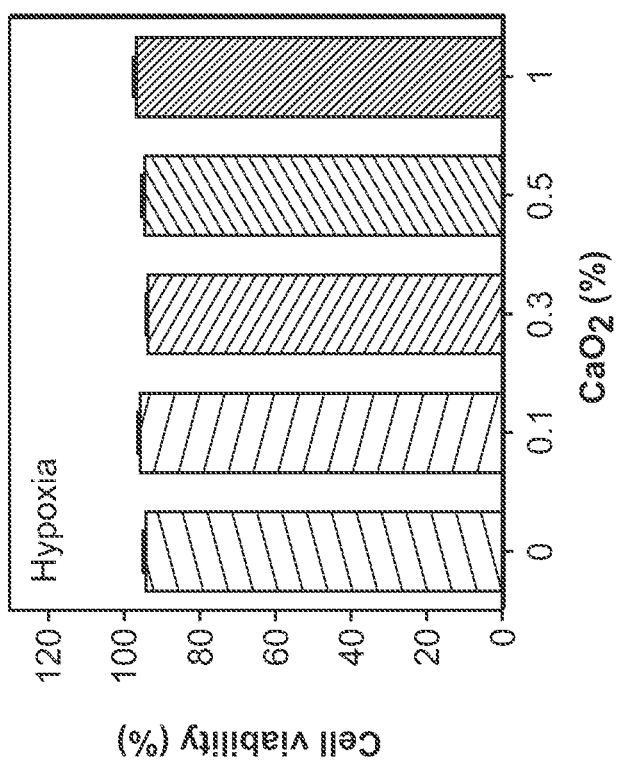
Figure 4A:
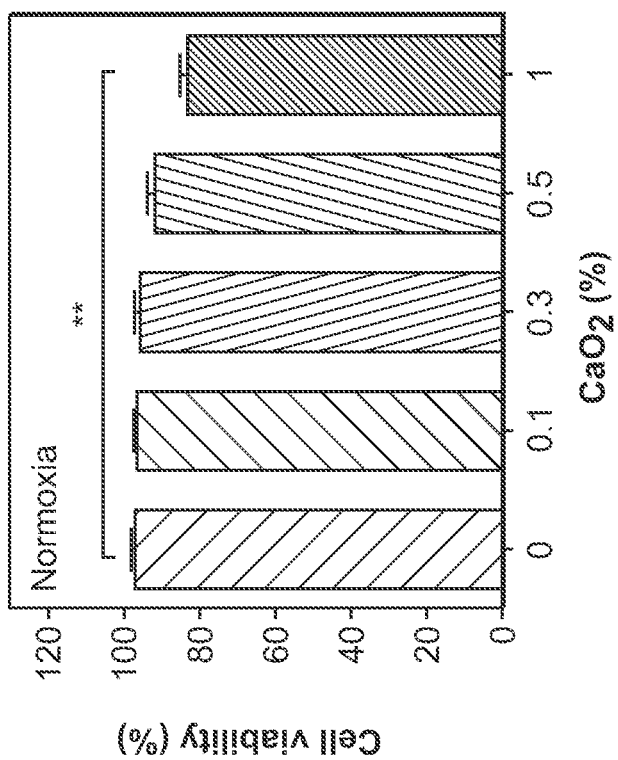
Figure 4C:
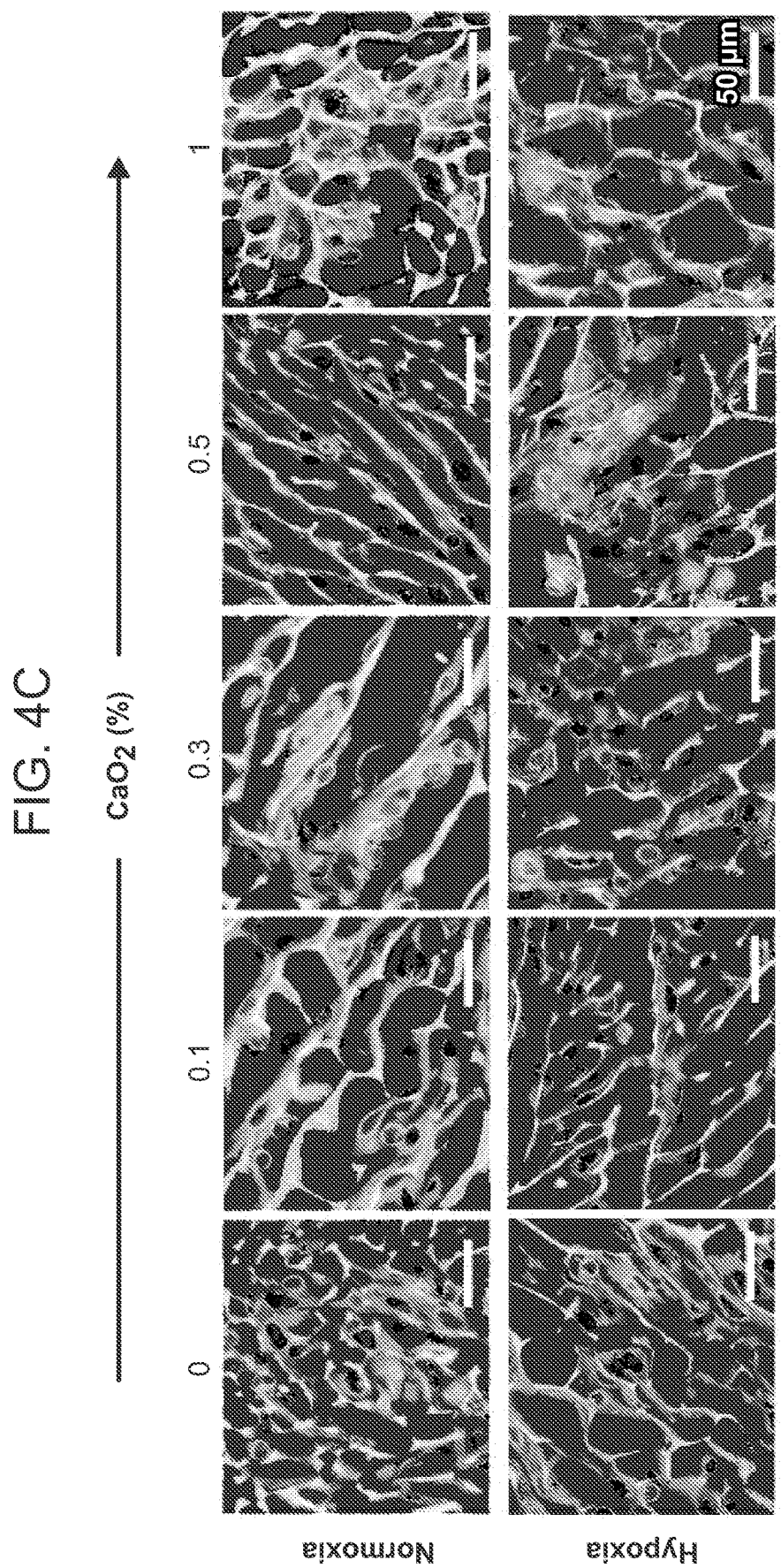

Cell viability was determined within $O_2$-cryogels as an indication of their cytocompatibility. Cryogels and $O_2$-cryogels were partially dehydrated, seeded with 1×10⁵ B16-F10 cells and incubated at 37° C. for 24 hr in normoxia (FIG. 4A and FIG. 4C) or hypoxia (FIG. 4B and FIG. 4C). In normoxia (FIG. 4A), $O_2$-cryogels were cytocompatible, as B16-F10 cell-laden scaffolds with 0% to 0.5% $CaO_2$ had a high viability (~97%), similar to control cryogels. In scaffolds that contained 1% $CaO_2$, a slight decrease of viability (85%±2%) was observed. However, regardless of the composition of $O_2$-cryogels, cells homogeneously attached and spread throughout the constructs (FIG. 4C). Similar results were obtained in hypoxia. The viability of B16-F10 cells remained high independently of the $CaO_2$ concentration (95±2%) (FIG. 4B) and no significant changes in cell attachment and spreading were observed (FIG. 4C). These results suggest that $O_2$-cryogels developed in this study are cytocompatible, promote cell adhesion, and retain cell viability in both, normoxic and hypoxic conditions.

To further investigate the biocompatibility of $O_2$-cryogels, catalase-free 1% $O_2$-cryogels and catalase-containing 1% $O_2$-cryogels (1% APC) were syringe delivered into the subcutaneous space of the dorsal flanks of C57BL/6J mice. Cryogels containing 1% APC were used as control. Seven days post injection, cryogels and $O_2$-cryogels were excised with the surrounding tissue and analyzed by histology (H&E and MT staining). All the explanted scaffolds demonstrated no change in size, absence of fibrosis, and minimal inflammation without the initiation of an immune reaction (FIG. 4D). Only a few neutrophils were observed within cryogels and $O_2$-cryogels containing 1% APC. Moreover, the junction between the connective tissue stroma and these cryogels was mainly constituted of fibrin suggesting the correct integration of the scaffolds within the native tissue. However, catalase-free 1% $O_2$-cryogels showed large numbers of neutrophils in the connective tissue stroma and over the surface of the implants. In addition, neutrophils and some fibrin are extending within these cryogels, suggesting a stronger connective tissue stromal response. Altogether, these results suggest that $O_2$-cryogels are injectable biomaterials, biocompatible, and that catalase successfully prevented a host inflammatory response.

Figure 5A:
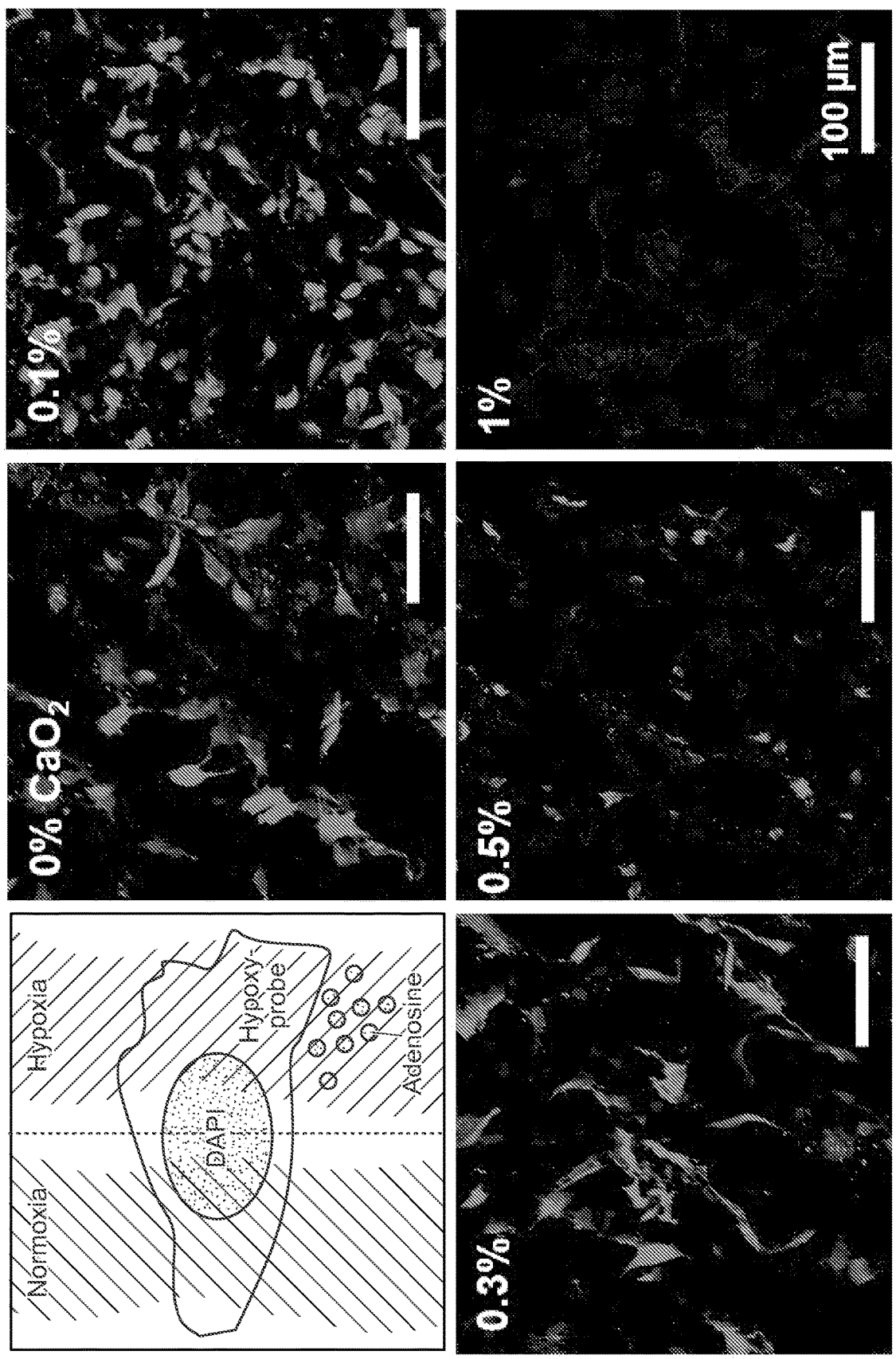
Figure 5C:
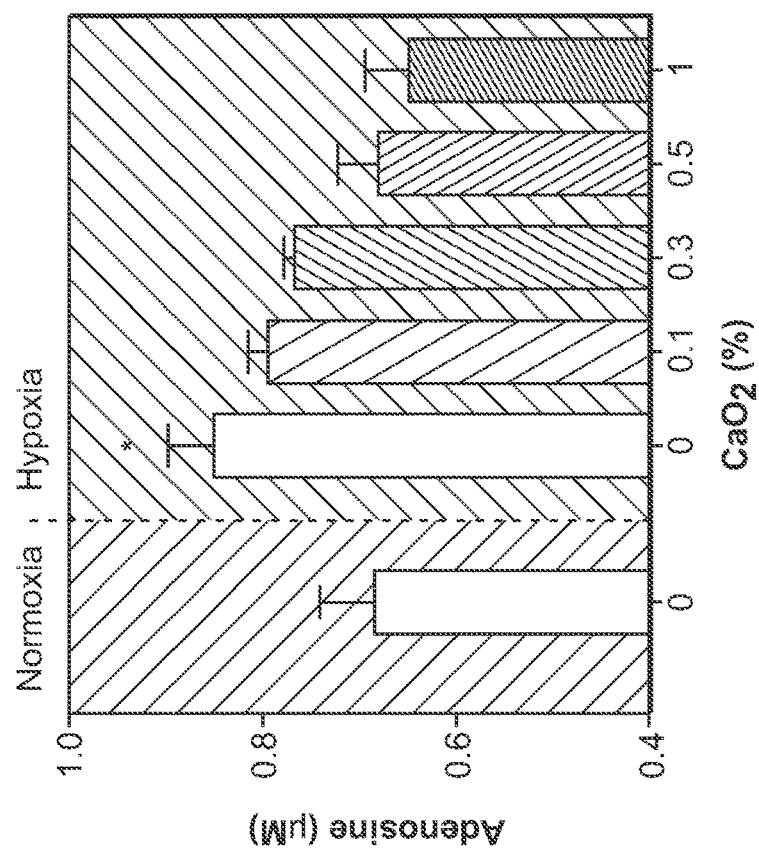
Figure 5B:
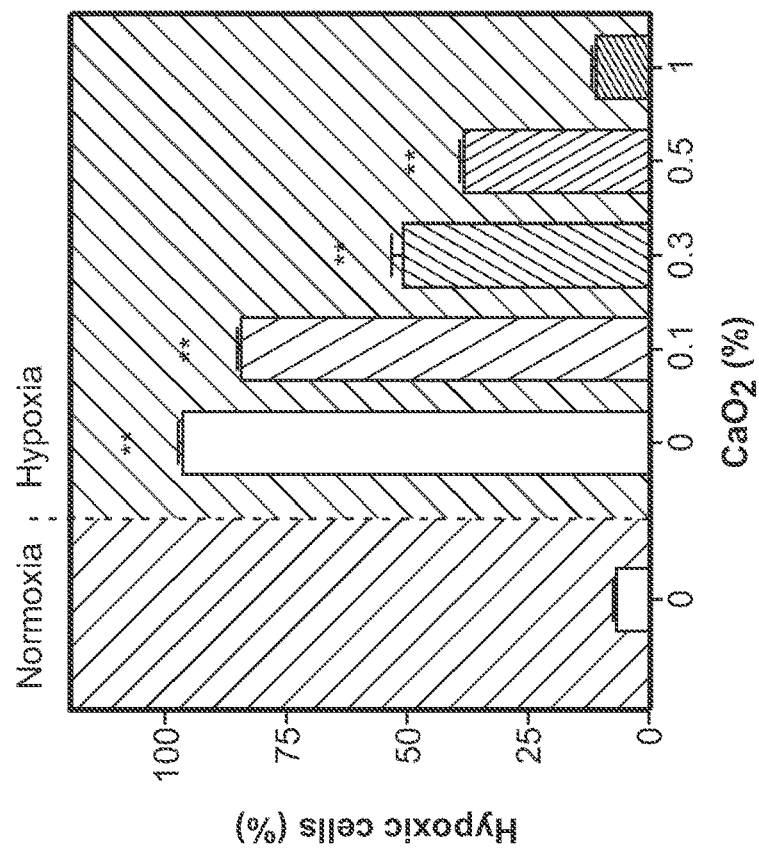

Example 5. Reversing Local Cellular Tumor Hypoxia and Associated Immunosuppressive Characteristics Cellular hypoxia within cryogels and $O_2$-cryogels was next assessed by analyzing the number of hypoxic B16-F10 cells within the scaffolds using hypoxyprobe (FIG. 5A-5B).

After 24 hr incubation in hypoxia, 96±1.2% of cells were hypoxic within control cryogels. Increasing the $CaO_2$ concentration within $O_2$-cryogels resulted in a significant reduction of hypoxic cells within the scaffolds with 84.5±0 0.6%, 50.7±1.7%, 37.9±0.7% and 10.7±0.6% of cell hypoxia for 0.1%, 0.3%, 0.5% and 1% $CaO_2$ respectively. Moreover, no significant difference was observed between cells cultured in hypoxia within 1% $O_2$-cryogels and cell cultures in normoxia within cryogels, suggesting a complete reversion of the hypoxic environment. The influence of reversing cell hypoxia was further analyzed after a 24 hr-incubation period by measuring the concentration of extracellular adenosine within the supernatant of cell-laden cryogels and $O_2$-cryogels (FIG. 5C).

As expected, cells cultured within cryogels in hypoxia showed an increased production of extracellular adenosine (0.85±0.05 µM) compared to normoxia (0.68±0.08 µM). However, in hypoxia, the increase of $CaO_2$ concentration within $O_2$-cryogels induced a significant decrease of extracellular adenosine concentration (0.1% $CaO_2$=0.79±0.02 µM; 0.3% $CaO_2$=0.76±0.01 µM), with values similar to normoxia with 0.5% and 1% $CaO_2$ (0.67±0.05 µM and 0.65±0.06 µM respectively). The impact of hypoxia reversion on the phenotype of B16-F10 cells was also investigated. Because a sudden change in oxygen concentration or cell toxicity can dramatically impact cell phenotype, only 0.5% $O_2$-cryogels that can provide sustained oxygen release over 30h without cell cytotoxicity have been investigated and compared to cryogels. B16-F10 cells were seeded within these scaffolds, cultured in normoxic or hypoxic conditions for 24 hr, then total mRNA was extracted from the cells and their gene expression profile was analyzed by RT-qPCR (FIG. 5D). When seeded in $CaO_2$-free cryogels under hypoxic conditions, B16-F10 cells showed an overexpression of hypoxia-inducible genes, more specifically HIF1α (+45%), Wnt11 (+123%), CD73 (+75%), VEGFα (+125%), CD44 (+140%), and CD133 (+246%).

However, 0.5% $O_2$-cryogels prevented any gene expression changes when B16-F10 cells were incubated in hypoxia. Similarly, to normoxic conditions, comparable expression levels of HIF1α, CD73, Wnt11, and VEGFα were observed for cells seeded in $O_2$-cryogels and incubated in hypoxic conditions (1% $O_2$) for 24 hr. Additionally, in comparison to $CaO_2$-free cryogels, $O_2$-cryogels downregulated cancer stem-like markers on B16-F10 cells as shown by a lower expression level of CD44 (−65%) and CD133 (−48%). Altogether, these results suggest that $O_2$-cryogels can reverse cellular hypoxia, suppress the accumulation of immunosuppressive metabolites such as extracellular adenosine, and prevent melanoma cells to acquire an aggressive phenotype.

Figure 6A:
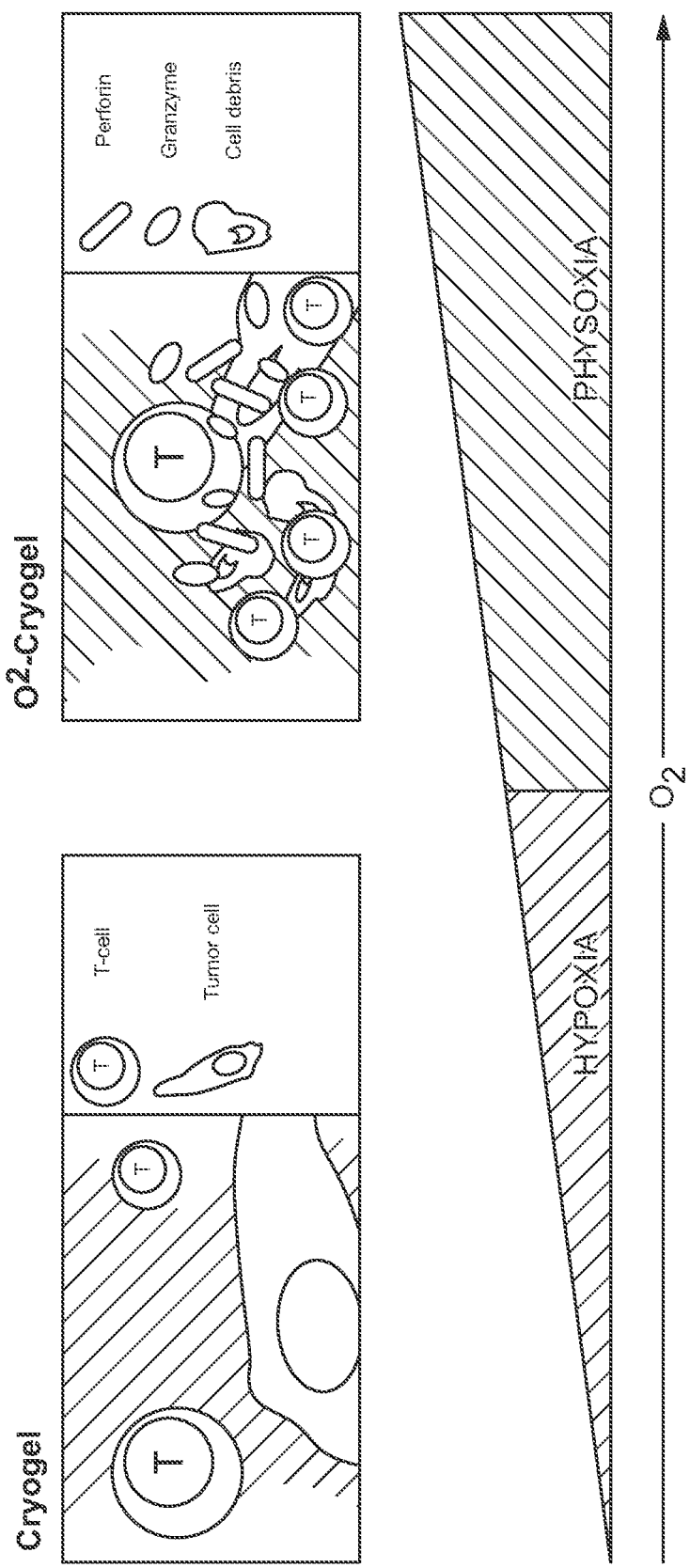
FIG. 6A-FIG. 6G depict $O_2$-cryogels rescue of T cell-mediated cytotoxicity against tumor cells.
Figure 6B:
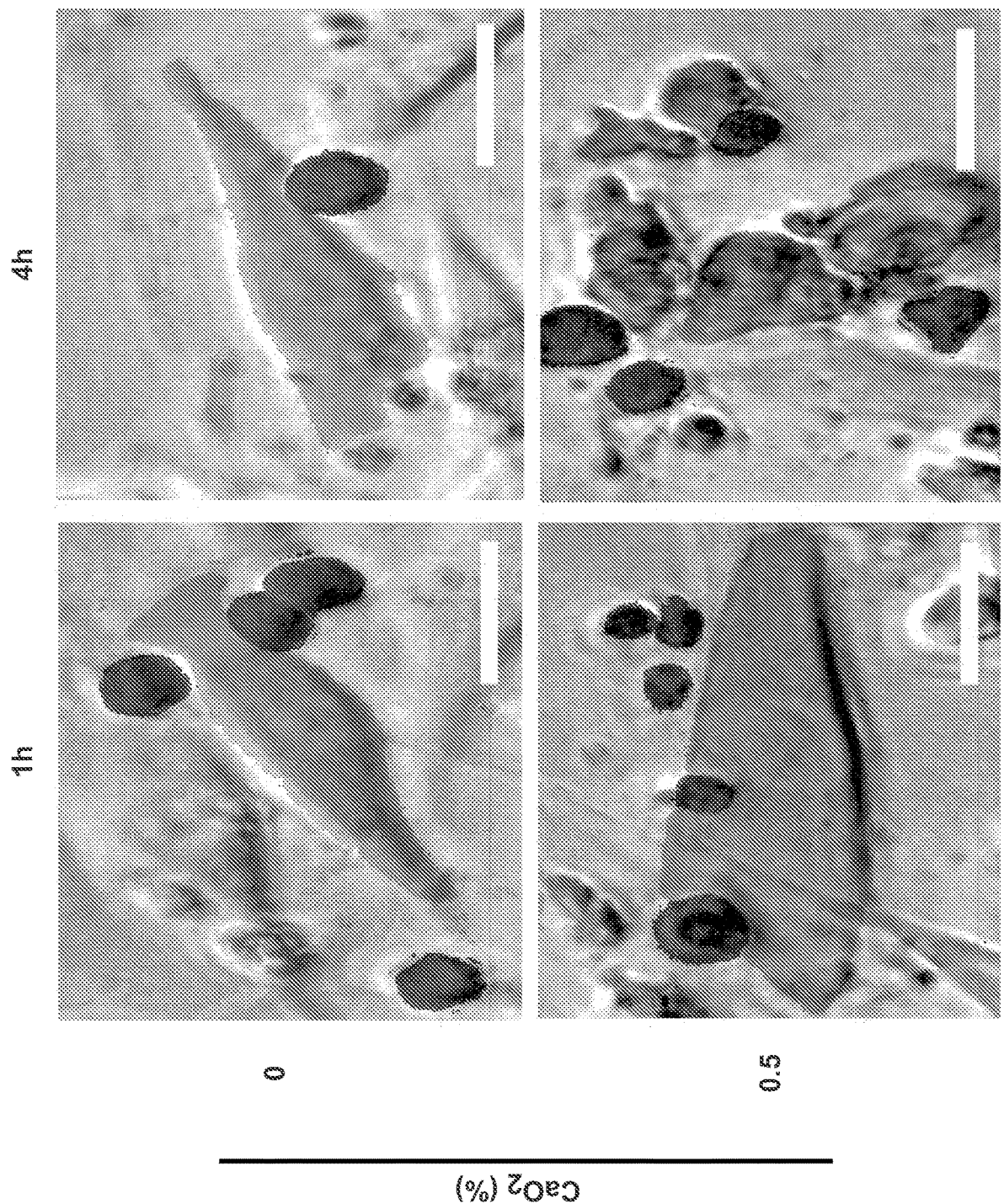
Figure 6C:
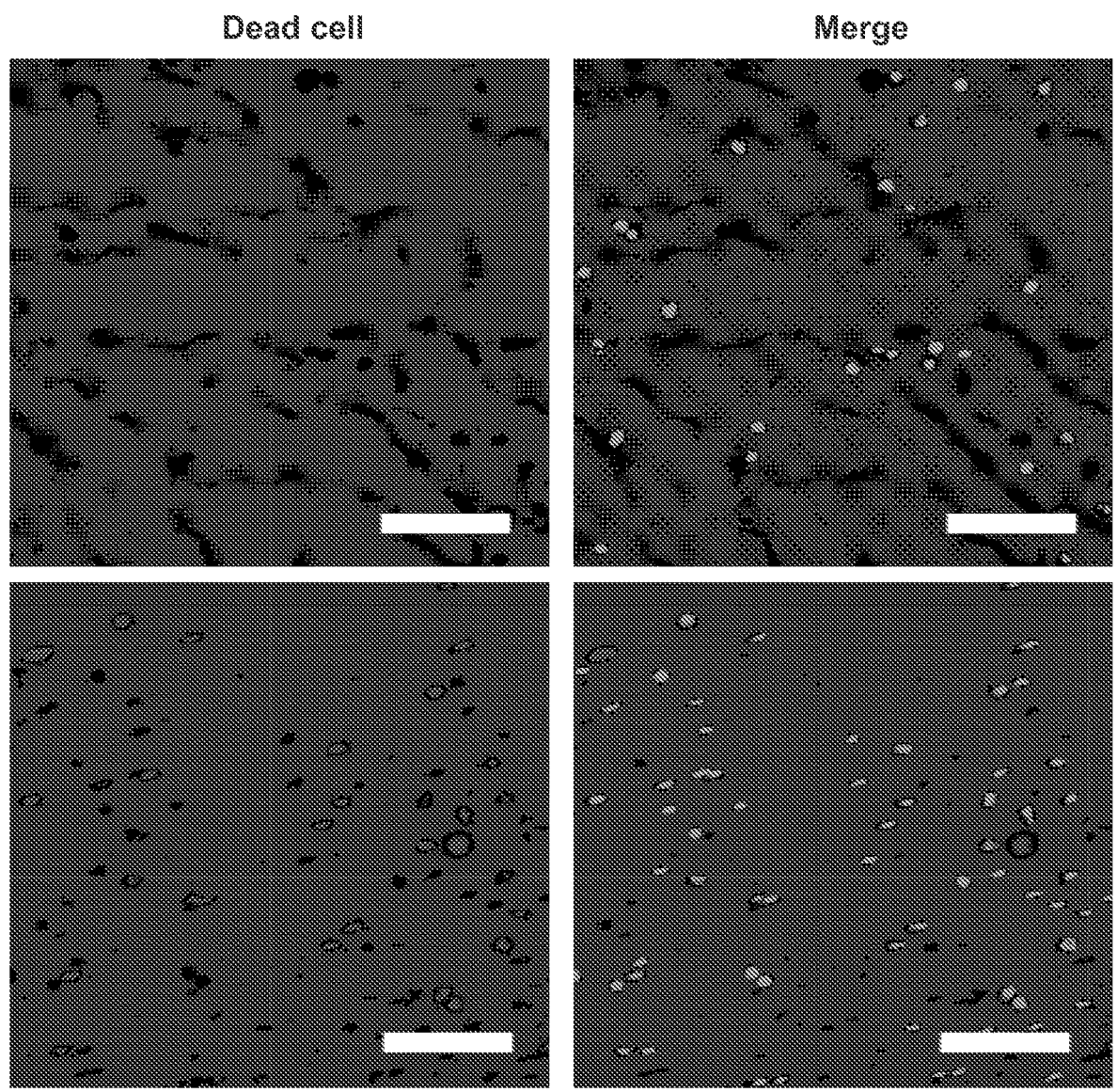

Example 6. Restored Cytotoxicity of OT-1 T Cells in an Antigen-Specific B16-Ova Model Recent studies have established that the hypoxic TME significantly impairs the ability of tumor-reactive T cells to kill tumor cells. Thus, the impact of $O_2$-cryogels on the capacity of spleen-derived ovalbumin (ova)-specific OT-1 T cells to kill B16-ova cells in normoxia or hypoxia was determined (FIG. 6A). Cytotoxic T cell function was first assessed in real time using time-lapse microscopy (1 picture every 10 min) (FIG. 6B). B16-ova cells were cultured for 3 hr in p24-well plates in normoxia to allow cell adhesion, prior to co-culture with OT-1 T cells for 4 hr in hypoxia in presence of cryogels or 0.5% $O_2$-cryogels. During this co-culture in hypoxic conditions, no tumor cell death induced by OT-1 T cells was observed in presence of $CaO_2$-free cryogels (FIG. 6B-FIG. 6C).

However, with 0.5% $O_2$-cryogels, OT-1 T cells were able to efficiently kill B16-ova tumor cells in only 4 hr (FIG. 6B). The effect of the $CaO_2$ concentration on the revitalization of T cell cytotoxicity in hypoxia as compared to normoxia was measured using confocal microscopy (FIG. 6C-FIG. 6D and FIG. 10 and FIG. 11A). B16-ova cells were cultured in cryogels or $O_2$-cryogels containing different concentrations of $CaO_2$ for 3 hr in normoxia before co-incubation with OT-1 splenocytes for 4 hr or 24 hr in normoxia or hypoxia. In normoxic conditions, OT-1 cytotoxic T cells were able to infiltrate within the scaffolds, as well as recognize and kill B16-ova cells (85±5% cytotoxicity) in only 4 hr (FIG. 11A) regardless of $CaO_2$ concentration. Coherently with the time-lapse experiments, in hypoxia, the cytotoxicity of OT-1 T cells within $CaO_2$-free cryogels was significantly lower (4 hr=3.55±1%; 24 hr=34.38±11%), confirming the inhibitory effect of low oxygen tension on the cytotoxic activity of T-cells (FIG. 5D and FIG. 11A). After 4 hr co-incubation in hypoxia, $O_2$-cryogels were able to restore up to 50% of cytotoxicity by OT-1 T cells in a $CaO_2$ concentration dependent manner (FIG. 11A).

Figure 6D:
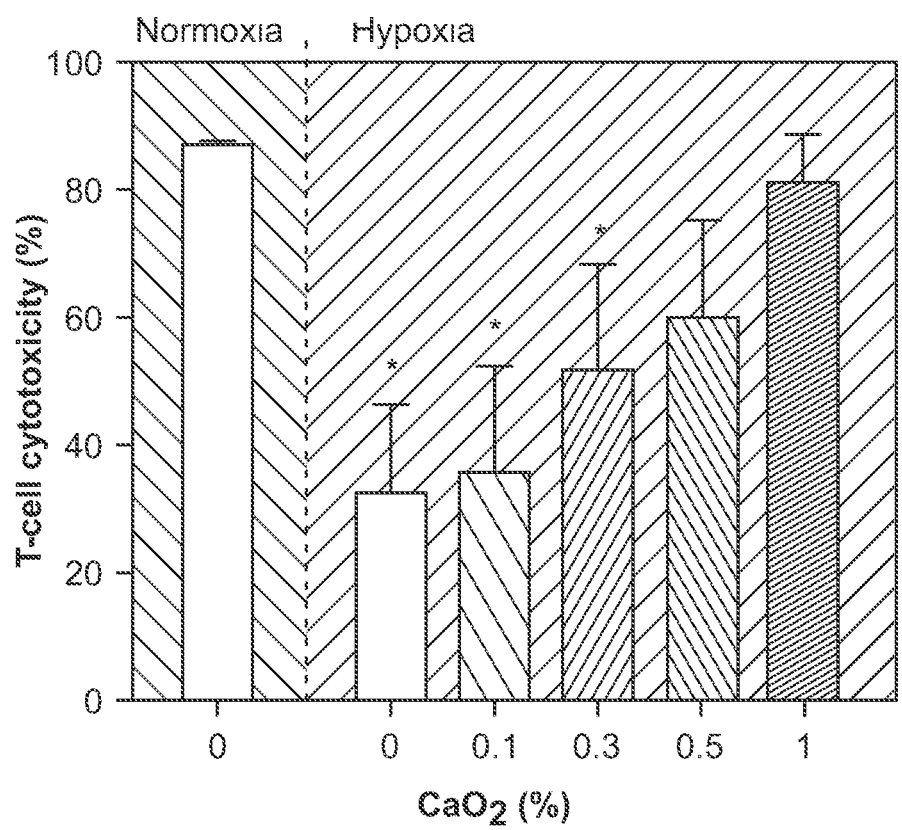
Figure 6E:
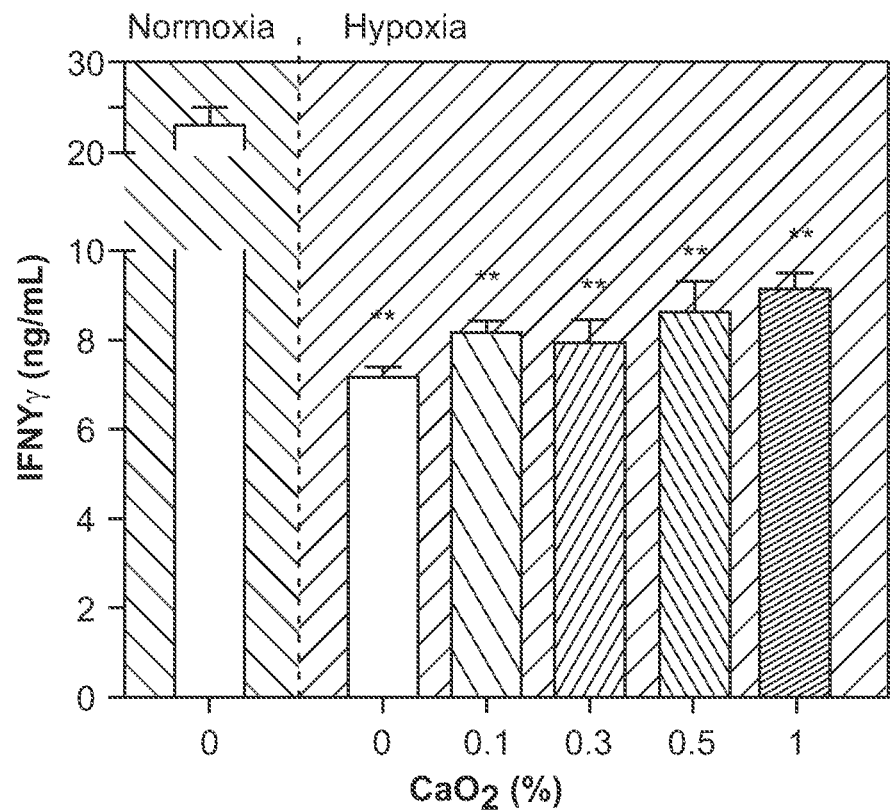
Figure 6F:
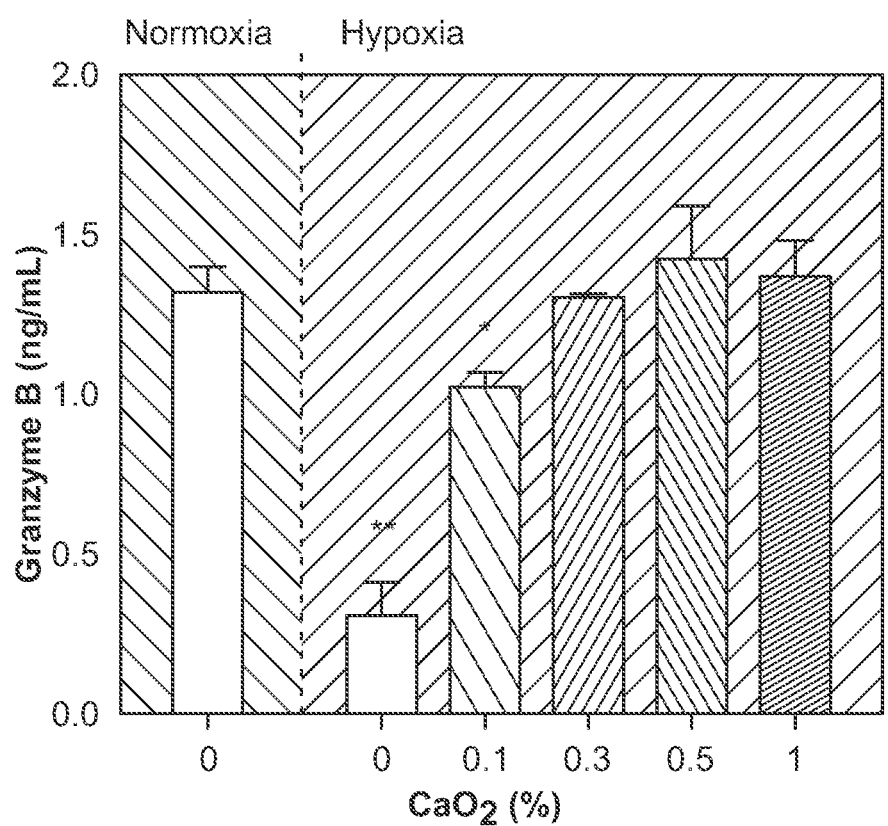
Figure 6G:
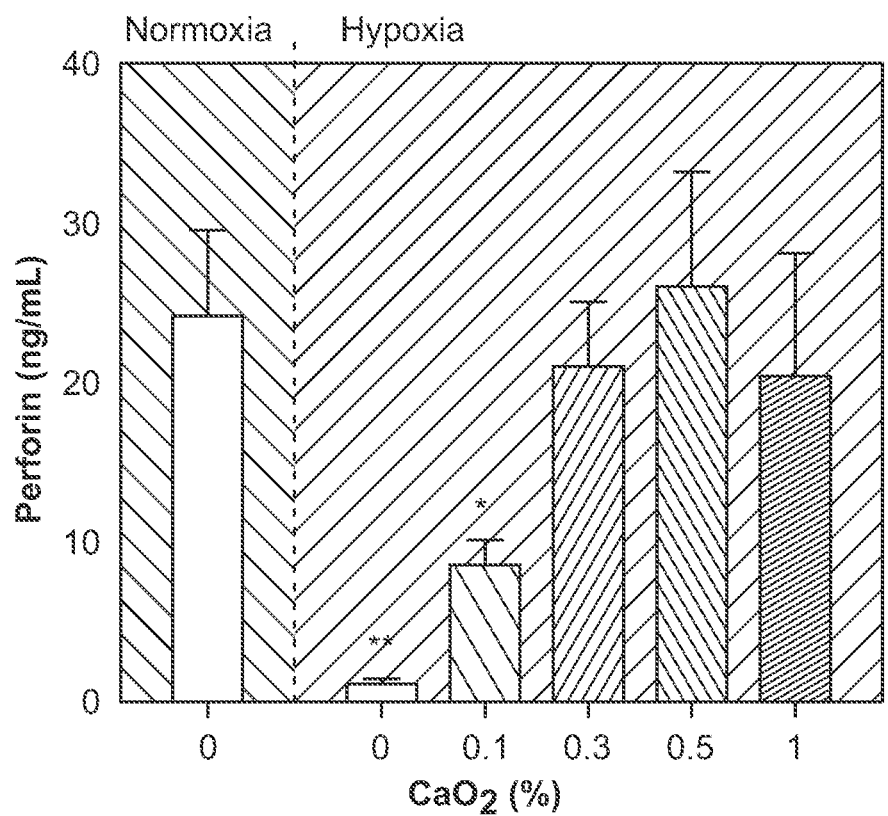

$O_2$-cryogels containing 0.5% and 1% $CaO_2$ particles were able to fully restore the cytotoxic activity of OT-1 T cells in hypoxia after 24 hr to levels that were similar to cells cultured in normoxia (FIG. 6D). This was further confirmed by evaluating the concentration of IFNγ, perforin and granzyme B secreted from functional OT-1 T cells after 4 hr (FIG. 11B-FIG. 11D) and 24 hr (FIG. 6E-FIG. 6G). In agreement with the cytotoxicity assays, IFNγ, perforin and granzyme-B concentrations in the supernatant of cell-laden cryogels were significantly reduced in hypoxia (60% to 95% inhibition) when compared to normoxic conditions. Although $O_2$-cryogels containing as low as 0.1% $CaO_2$ had limited impact after 4 hr, they were able to partially suppress hypoxia-driven inhibition of perforin (60% vs 95% inhibition) and granzyme-B (30% vs 60%) secretion after 24 hr. In addition, cryogels containing higher amounts of $CaO_2$ completely restored the capability of T cells to secrete perforin and granzyme-B, the two main molecules involved in inducing apoptosis and cytotoxicity of targeted B16-ova cells, after 24 hr.

Overall, these results indicate that $O_2$-cryogels can locally reverse hypoxia, bypass T cell inhibition, and reactivate tumor cell cytotoxicity via secretion of pro-inflammatory cytokines and protein toxins such as perforin and granzyme B.

Example 7: In Vitro Dendritic Cell (DC) Activation Assay

Figure 12A:
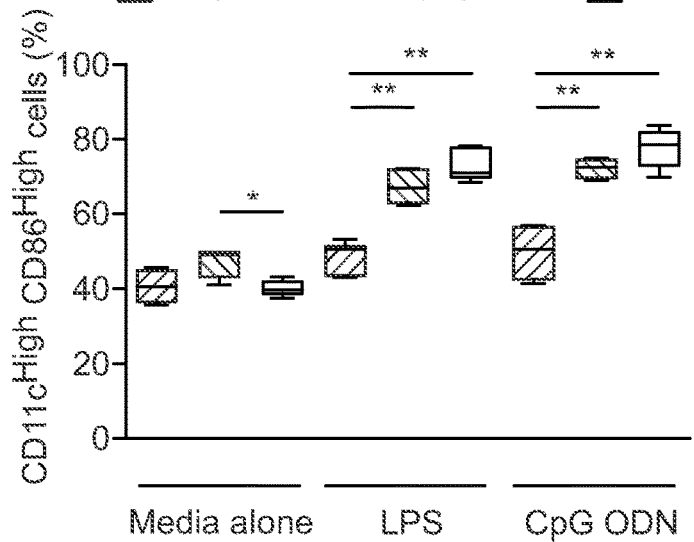
FIG. 12A-FIG. 12F depict BMDC cellular markers in hypoxic, hypoxic with an $O_2$-cryogel, and normoxic conditions in the presence of media, lipopolysaccharide (LPS) or CpG oligodeoxynucleotides (CpG ODN) 1826.
Figure 12B:
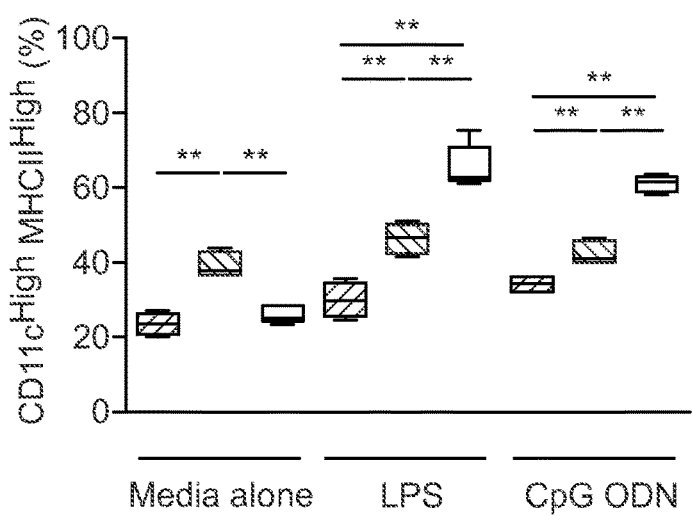
Figure 12C:
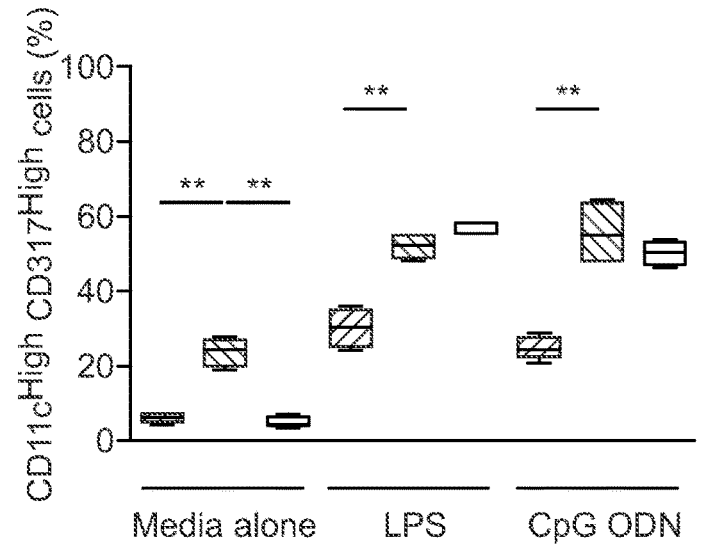
Figure 12D:
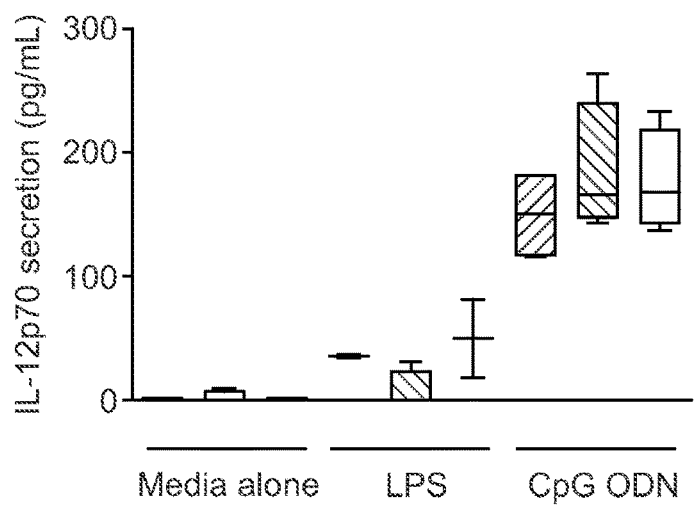
Figure 12E:
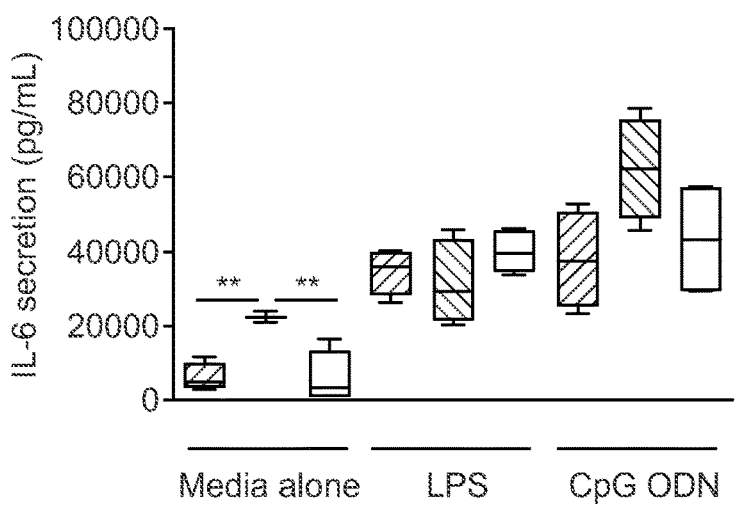
Figure 12F:
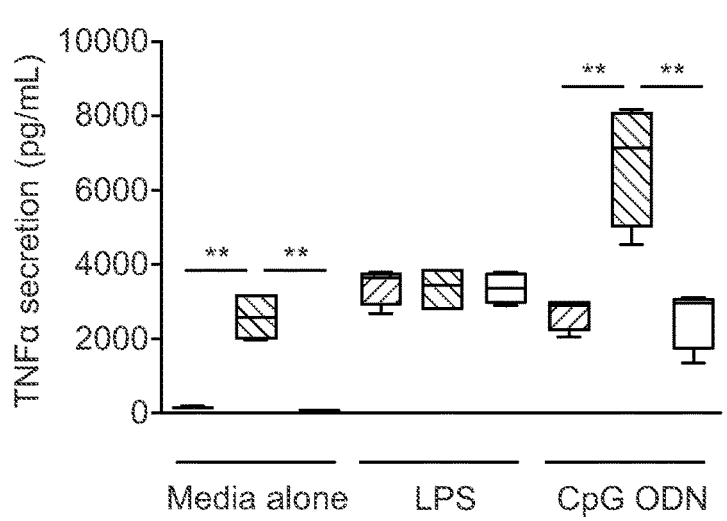

The in vitro dendritic cell (DC) activation assay was performed as described above. FIG. 12A-12C illustrate BMDC cellular markers in hypoxic, hypoxic with an $O_2$-cryogel, and normoxic conditions in the presence of media, LPS or CpG ODN. After a 24 hr incubation period, expression of maturation markers CD86 (FIG. 12A), MHCII (FIG. 12B) and CD317 (FIG. 12C) on BMDCs (CD11c—positive cells) were assessed. Similarly, secretions of IL-12p70 (FIG. 12D), IL-6 (FIG. 12E) and TNFα (FIG. 12F) in the supernatant were quantified to evaluate the extent of BMDC activation. Unlike in normoxia, hypoxia prevented BMDC activation when cultured with two adjuvants (i.e., LPS and CpG-ODN 1826). However, $O_2$-cryogels were able to restore the capacity of BMDCs to be activated in hypoxic conditions, enabling upregulation of cellular activation markers and proinflammatory cytokine secretion similar to normoxic conditions. This set of data supports that supplemental oxygen delivery from cryogels rescued immune cell function and activity. Also, these results suggest the potential of $O_2$-cryogel as a promising vaccination platform. Once activated, DCs can migrate out of cryogels, travel to the closest draining lymph nodes, prime antigen-specific T cells, and ultimately mount an immune response.

FIG. 13 shows increasing $CaO_2$ concentration within $O_2$-cryogels from 1 to 2% improved both the maximum oxygen concentration and the sustained release of oxygen from $O_2$-cryogels. In normoxia, 2% $O_2$-cryogels induced a maximum oxygen concentration increase by 40% as compared to 1% $O_2$-cryogels. In addition, 2% $O_2$-cryogels allowed a sustained release of oxygen up to ~96 hr.

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

The invention claimed is:

1. A method of reducing hypoxia in a biological tissue, comprising administering to the biological tissue an oxygen-generating cryogel, wherein the administration is by injection, catheter, or surgery; and the cryogel comprises:
   i) a lyoprotectant;
   ii) a peroxide, an oxide or a percarbonate;
   iii) a catalase, wherein the catalase is acrylate-PEG-catalase; and
   iv) polymerized hyaluronic acid.

2. The method of claim 1, wherein the cryogel further comprises G4RDGSP; wherein the G4RDGSP is conjugated to the cryogel.

3. The method of claim 2, wherein the polymerized hyaluronic acid is comprised by polymerized hyaluronic acid glycidyl methacrylate, the G4RDGSP is comprised by acrylate-PEG-G4RDGSP, and the peroxide, oxide or percarbonate is $CaO_2$.

4. The method of claim 1, wherein the lyoprotectant is selected from sucrose, trehalose, and mannitol.

5. The method of claim 1, wherein the cryogel further comprises one or more checkpoint inhibitors selected from one or more adenosine receptor antagonists for A2a, A2b or A3 receptors, anti-CTLA4, anti-CD73, anti-PD1, and anti-PD-L1.

6. The method of claim 1, wherein the cryogel has a mean size of 1 µm to 10 cm, 10 µm to 10 mm, 50 µm to 2 mm, 1 µm to 5 mm, 1 µm to 2 mm, or 5 µm to 500 µm.

7. The method of claim 1, wherein the hypoxia is reduced such that oxygen tissue tension is higher than 5% oxygen.

8. The method of claim 1, wherein the cryogel releases oxygen for at least about 4 hours, at least about 16 hours, at least about 24 hours, at least about 48 hours, or at least about 96 hours.

9. The method of claim 1, wherein the cryogel increases oxygen concentration in the biological tissue to physioxic or normoxic levels.

10. The method of claim 1, wherein hypoxia-induced immunosuppression of one or more of T cells, B cells, and myeloid cells is reduced or reversed compared to immunosuppression levels in hypoxic biological tissue.

11. The method of claim 1, wherein extracellular adenosine concentration in hypoxic biological tissue decreases to levels present in normoxic biological tissue.

12. The method of claim 1, wherein the biological tissue is a solid tumor selected from melanoma, renal cell carcinoma, prostate cancer, breast cancer, lung cancer, pancreatic cancer, glioblastoma, ovarian cancer, colon cancer, sarcoma, nasopharyngeal cancer, head and neck cancer, and lymphoma.

13. The method of claim 1, wherein the peroxide, oxide or percarbonate is calcium peroxide or magnesium peroxide.

14. The method of claim 1, wherein the peroxide, oxide or percarbonate is encapsulated $H_2O_2$/polyvinylpyrrolidone or hydrogen peroxide.

15. The method of claim 1, wherein the peroxide, oxide or percarbonate is sodium percarbonate.

16. The method of claim 1, wherein the peroxide, oxide or percarbonate is zinc oxide or manganese dioxide.

17. The method of claim 3, wherein the lyoprotectant is selected from sucrose, trehalose, and mannitol.

18. The method of claim 2, wherein the G4RDGSP is comprised by acrylate-PEG-G4RDGSP.

19. The method of claim 1, wherein the polymerized hyaluronic acid is comprised by polymerized hyaluronic acid glycidyl methacrylate.

20. The method of claim 1, wherein the cryogel further comprises one or more adenosine receptor antagonists selected from the group consisting of ZM241385, 1,7-methylxantine, theophylline, theobromine, 7-(2-phenylethyl)-5-amino-2-(2-furyl)-pyrazolo-[4,3-e]-1,2,4-triazolo[1,5-c]pyrimidine], and (E)-1,3-diethyl-8-(3,4-dimethoxystyryl)-7-methyl-3,7-dihydro-1H-purine-2,6-dione.

21. The method of claim 3, wherein the cryogel further comprises
   (i) one or more checkpoint inhibitors selected from one or more adenosine receptor antagonists for A2a, A2b or A3 receptors, anti-CTLA4, anti-CD73, anti-PD1, and anti-PD-L1; or
   (ii) one or more adenosine receptor antagonists selected from the group consisting of ZM241385, 1,7-methylxantine, theophylline, theobromine, 7-(2-phenylethyl)-5-amino-2-(2-furyl)-pyrazolo-[4,3-e]-1,2,4-triazolo[1,5-c]pyrimidine], and (E)-1,3-diethyl-8-(3,4-dimethoxystyryl)-7-methyl-3,7-dihydro-1H-purine-2,6-dione.

* * * * *